United States Patent
High et al.

(10) Patent No.: US 11,408,899 B2
(45) Date of Patent: Aug. 9, 2022

(54) AAV VECTOR AND ASSAY FOR ANTI-AAV (ADENO-ASSOCIATED VIRUS) NEUTRALIZING ANTIBODIES

(71) Applicant: THE CHILDREN'S HOSPITAL OF PHILADELPHIA, Philadelphia, PA (US)

(72) Inventors: Katherine A. High, Merion Station, PA (US); Federico Mingozzi, Paris (FR); Yifeng Chen, Philadelphia, PA (US)

(73) Assignee: THE CHILDREN'S HOSPITAL OF PHILADELPHIA, Philadelphia, PA (US)

(*) Notice: Subject to any disclaimer, the term of this patent is extended or adjusted under 35 U.S.C. 154(b) by 0 days.

(21) Appl. No.: 14/904,205

(22) PCT Filed: Jul. 11, 2014

(86) PCT No.: PCT/US2014/046428
§ 371 (c)(1),
(2) Date: Jan. 11, 2016

(87) PCT Pub. No.: WO2015/006743
PCT Pub. Date: Jan. 15, 2015

(65) Prior Publication Data
US 2016/0123990 A1    May 5, 2016

Related U.S. Application Data

(60) Provisional application No. 61/845,841, filed on Jul. 12, 2013.

(51) Int. Cl.
| | | |
|---|---|---|
| *G01N 33/68* | (2006.01) |
| *C12N 15/86* | (2006.01) |
| *C12Q 1/70* | (2006.01) |
| *C12Q 1/6897* | (2018.01) |
| *C12N 7/00* | (2006.01) |
| *A61K 48/00* | (2006.01) |

(52) U.S. Cl.
CPC .......... *G01N 33/6854* (2013.01); *C12N 7/00* (2013.01); *C12N 15/86* (2013.01); *C12Q 1/6897* (2013.01); *C12Q 1/701* (2013.01); *A61K 48/00* (2013.01); *C12N 2750/14131* (2013.01); *C12N 2750/14143* (2013.01); *G01N 2333/075* (2013.01); *G01N 2333/90241* (2013.01); *G01N 2469/20* (2013.01)

(58) Field of Classification Search
CPC ......... G01N 33/6854; G01N 2333/075; G01N 2333/90241; G01N 2469/20; C12N 7/00; C12N 15/86; C12N 2750/14131; C12N 2750/14143; C12Q 1/6897; C12Q 1/701; A61K 48/00

See application file for complete search history.

(56) References Cited

U.S. PATENT DOCUMENTS

| | | |
|---|---|---|
| 2005/0233457 A1 | 10/2005 | Block |
| 2008/0050343 A1 | 2/2008 | Wilson et al. |
| 2008/0166758 A1 | 7/2008 | Englehardt et al. |
| 2012/0083001 A1 | 4/2012 | Suzuki et al. |

FOREIGN PATENT DOCUMENTS

| | | |
|---|---|---|
| CN | 103014064 A | 3/2013 |
| JP | 2002-529098 A | 9/2002 |
| JP | 2003-511037 A | 3/2003 |
| JP | 2004-500858 A | 1/2004 |
| JP | 2006-505249 A | 2/2006 |
| RU | 2375456 C2 | 6/2003 |
| WO | 2001/92551 A2 | 12/2001 |
| WO | 2003/104485 A2 | 12/2003 |
| WO | 2010/129021 A1 | 11/2010 |
| WO | 2012/042684 A1 | 4/2012 |
| WO | 2012112578 A2 | 8/2012 |
| WO | 2012/061529 A1 | 5/2013 |
| WO | 2012/061530 A1 | 5/2013 |
| WO | 2013/078400 A1 | 5/2013 |

OTHER PUBLICATIONS

Rapti K, Louis-Jeune V, Kohlbrenner E, Ishikawa K, Ladage D, Zolotukhin S, Hajjar RJ, Weber T. Neutralizing antibodies against AAV serotypes 1, 2, 6, and 9 in sera of commonly used animal models. Mol Ther. Jan. 2012;20(1):73-83. Epub Sep. 13, 2011.*
Wang Z, Ma HI, Li J, Sun L, Zhang J, Xiao X. Rapid and highly efficient transduction by double-stranded adeno-associated virus vectors in vitro and in vivo. Gene Ther. Dec. 2003;10(26):2105-11.*
Mingozzi F, Chen Y, Edmonson SC, Zhou S, Thurlings RM, Tak PP, High KA, Vervoordeldonk MJ. Prevalence and pharmacological modulation of humoral immunity to AAV vectors in gene transfer to synovial tissue. Gene Ther. Apr. 2013;20(4):417-24. Epub Jul. 12, 2012.*
Murphy SL, Li H, Zhou S, Schlachterman A, High KA. Prolonged susceptibility to antibody-mediated neutralization for adeno-associated vectors targeted to the liver. Mol Ther. Jan. 2008;16(1):138-45. Epub Oct. 23, 2007. Erratum in: Mol Ther. Mar. 2008;16(3):633.*
Hösel M, Broxtermann M, Janicki H, Esser K, Arzberger S, Hartmann P, Gillen S, Kleeff J, Stabenow D, Odenthal M, Knolle P, Hallek M, Protzer U, Büning H. Toll-like receptor 2-mediated innate immune response in human nonparenchymal liver cells toward adeno-associated viral vectors. Hepatology. Jan. 2012;55(1):287-97.*

(Continued)

*Primary Examiner* — Rachel B Gill
(74) *Attorney, Agent, or Firm* — Pillsbury Winthrop Shaw Pittman LLP; Robert M. Bedgood

(57) ABSTRACT

Virus vectors, virus particles, and methods and uses of screening for, detecting, analyzing and determining amounts of virus antibody, or neutralizing antibody activity of samples are provided. Such virus vectors, virus particles, and methods and uses are applicable to a broad range of virus types, such as lentiviruses, adenovirus, and adeno-associated virus (AAV) serotypes. Methods and uses include virus antibody screening, such as anti-virus immunoglobulins screened for, detected, analyzed and amounts determined.

34 Claims, 5 Drawing Sheets

Specification includes a Sequence Listing.

(56) References Cited

OTHER PUBLICATIONS

Martin PT, Xu R, Rodino-Klapac LR, Oglesbay E, Camboni M, Montgomery CL, Shontz K, Chicoine LG, Clark KR, Sahenk Z, Mendell JR, Janssen PM. Am J Physiol Cell Physiol. Mar. 2009;296(3):C476-88. Epub Dec. 24, 2008.*
Manno CS, et. al. Successful transduction of liver in hemophilia by AAV-Factor IX and limitations imposed by the host immune response. Nat Med. Mar. 2006;12(3):342-7. Epub Feb. 12, 2006.*
Clark KR. Recent advances in recombinant adeno-associated virus vector production. Kidney Int. Jan. 2002;61(1 Suppl):S9-15.*
Ellis BL, Hirsch ML, Barker JC, Connelly JP, Steininger RJ 3rd, Porteus MH. A survey of ex vivo/in vitro transduction efficiency of mammalian primary cells and cell lines with Nine natural adeno-associated virus (AAV1-9) and one engineered adeno-associated virus serotype. Virol J. Mar. 6, 2013;10:74.*
Meliani A, Leborgne C, Triffault S, Jeanson-Leh L, Veron P, Mingozzi F. Determination of anti-adeno-associated virus vector neutralizing antibody titer with an in vitro reporter system. Hum Gene Ther Methods. Apr. 2015;26(2):45-53.*
Allen JM, Halbert CL, Miller AD. Improved adeno-associated virus vector production with transfection of a single helper adenovirus gene, E4orf6. Mol Ther. Jan. 2000;1(1):88-95.*
Nevels M, Rubenwolf S, Spruss T, Wolf H, Dobner T. Two distinct activities contribute to the oncogenic potential of the adenovirus type 5 E4orf6 protein. J Virol. Jun. 2000;74(11):5168-81.*
Xie Q, Bu W, Bhatia S, Hare J, Somasundaram T, Azzi A, Chapman MS. RecName: Full=Capsid protein VP1 UniProtKB/Swiss-Prot: P03135.2. Updated Jul. 18, 2018, Dep. Apr. 23, 1993.*
Qing K, Li W, Zhong L, Tan M, Hansen J, et. al Adeno-associated virus type 2-mediated gene transfer: role of cellular T-cell protein tyrosine phosphatase in transgene expression in established cell lines in vitro and transgenic mice in vivo. J Virol. Feb. 2003;77(4):2741-6.*
Duong TT, Lim J, Vasireddy V, Papp T, Nguyen H, Leo L, Pan J, Zhou S, Chen HI, Bennett J, Mills JA. Comparative AAV-eGFP Transgene Expression Using Vector Serotypes 1-9, 7m8, and 8b in Human Pluripotent Stem Cells, RPEs, and Human and Rat Cortical Neurons. Stem Cells Int. Jan. 17, 2019;2019:7281912. eCollection 2019.*
Calcedo R, Wilson JM. AAV Natural Infection Induces Broad Cross-Neutralizing Antibody Responses to Multiple AAV Serotypes in Chimpanzees. Hum Gene Ther Clin Dev. Jun. 2016;27(2):79-82.*
Li P, Boenzli E, Hofmann-Lehmann R, Helfer-Hungerbuehler AK. Pre-existing antibodies to candidate gene therapy vectors (adeno-associated vector serotypes) in domestic cats. PLoS One. Mar. 21, 2019;14(3):e0212811. eCollection 2019.*
Vandamme C, Adjali O, Mingozzi F. Unraveling the Complex Story of Immune Responses to AAV Vectors Trial After Trial. Hum Gene Ther. Nov. 2017;28(11):1061-1074.*
McCarty DM, Fu H, Monahan PE, Toulson CE, Naik P, Samulski RJ. Adeno-associated virus terminal repeat (TR) mutant generates self-complementary vectors to overcome the rate-limiting step to transduction in vivo. Gene Ther. Dec. 2003;10(26):2112-8.*
Martino AT, Herzog RW, Anegon I, Adjali O. Measuring immune responses to recombinant AAV gene transfer. Methods Mol Biol. 2011;807:259-72.*
Boutin S, Monteilhet V, Veron P, Leborgne C, Benveniste O, Montus MF, Masurier C. Prevalence of serum IgG and neutralizing factors against adeno-associated virus (AAV) types 1, 2, 5, 6, 8, and 9 in the healthy population: implications for gene therapy using AAV vectors. Hum Gene Ther. Jun. 2010;21(6):704-12.*
Montefiori Lab. "Protocol for Measuring Neutralizing Antibodies Against HIV-1, SIV and SHIV Using a Luciferase Reporter Gene Assay in TZM-BL Cells." Jan. 2007, https://www.hiv.lanl.gov/content/nab-reference-strains/html/Clade-C/TZM-bl_Assay-SOP_Jan2007.pdf.*
Sprangers MC, Lakhai W, Koudstaal W, Verhoeven M, Koel BF, Vogels R, Goudsmit J, Havenga MJ, Kostense S. Quantifying adenovirus-neutralizing antibodies by luciferase transgene detection: addressing preexisting immunity to vaccine and gene therapy vectors. J Clin Microbiol. Nov. 2003;41(11):5046-52.*
Capsid protein VP1, Adeno-associated virus-8. Acc. No. Q6JC62, Dep. Jul. 5, 2004.*
Hu, Chuhong, et al, RH10 Provides Superior Transgene Expression in Mice When Compared With Natural AAV Serotypes for Neonatal Gene Therapy, J. Gene Med., 2010, 12(9):766-778.
McCarty, Douglas, M., Self-Complementary AAV Vectors: Advances and Applications, Mol. Ther., 2008, 16K10):1648-1656.
Wang, Xu-Shan, et al., Adeno-Associated Virus Type 2 DNA Replication in vivo: Mutation Analysis of the D Sequence in Viral Inverted Terminal Repeats, Journal of Virology, Apr. 1997, pp. 3077-3082.
Dwaipayan, S., et al., Targeted Modifications in Adeno-Associated Virus Serotype 8 Capsid Improves Its Hepatic Gene Transfer Efficiency In Vivo, Human Gene Therapy Methods, 2013, 24(2):104-116.
Boutin, Prevalence of Serum IgG and Neutralizing Factors Against Adeno-Associated Virus (AAV) Types 1, 2, 5, 6, 8, and 9 in the Healthy Population: Implications for Gene Therapy Using AAV Vectors, Human Gene Therapy, 2010, 21:704-712.
Kay, M.A., Evidence for Gene Transfer and Expression of Factor IX in Haemophilia B Patients Treated With an AAV Vector, Nature Genetics, 2000, 24:257-261.
Calcedo, R., et al., AAV Natural Infection Broad Cross-Neutralizing Antibody Responses to Multiple AAV Serotypes in Chimpanzees, Human Gene Therapy Clinical Development, 2016, 27(2):79-82.
McCarty, D.M., et al., Self-complementary recombinant adeno-associated virus (scAAV) vectors promote efficient transduction independently of DNA synthesis, Gene Therapy, 2001, 8:1248-1254.
Wikipedia Contributors, 'Adeno-associated virus', Wikipedia, The Free Encyclopedia, Jun. 30, 2013, 17:21 UTC, <https://en.wikipedia.org/w/index.php?title=Adeno-associated_virus&oldid=562771876> [accessed Aug. 28, 2020].
Calcedo, R., et al., Worldwide Epidemiology of Neutralizing Antibodies to Adeno-Associated Viruses, The Journal of Infectious Diseases, 2009, 199:381-390.
Sen, D., et al., Targeted Modifications in Adeno-Associated Virus Serotype 8 Capsid Improves Its Hepatic Gene Transfer Efficiency In Vivo, Human Gene Therapy Methods, 2013, 24:104-116.
European Patent Application No. 14 823 769.6, Communication pursuant to Rule 114(2) EPC, Third-Party Observations dated Nov. 23, 2021.
Genbank, NCBI Reference Sequence: NC_001401.2 [https://www.ncbi.nih.gov/nuccore/110645916 [downloaded Nov. 23, 2021, 11:49].
European Patent Application No. 14 823 769.6, Communication pursuant to Rule 114(2) EPC, Third-Party Observation dated Oct. 26, 2021.
Manning, W.C., et al., Transient Immunosupression Allows Transgene Expression Following Readministration of Adeno-Associated Viral Vectors, Human Gene Therapy, Mar. 1, 1998, 9:477-485.
Nathwani, A.C., et al., Factors influencing in vivo transduction by recombinant adeno-associated viral vectors expressing the human factor IX cDNA, Blood, Mar. 1, 2001 vol. 97, No. 5.
Paulmuruga, R, & Gambhir, S., Firefly Luciferase Enzyme Fragment Complementation for Imaging in Cells and Living Animals, Anal Chem., Mar. 1, 2005, 77(5):1295-1302.
European Patent Application No. 14 823 769.6, Communication pursuant to Rule 114(2) EPC, Third-Party Observation dated Nov. 11, 2021.
Nathwani, A.C., et al., Safe and efficient transduction of the liver after peripheral vein infusion of self-complementary AAV vector results in stable therapeutic expression of human FIX in nonhuman primates, Blood, Feb. 15, 2007, 109(4):1414-1421.
Synthego, HEK293 Cells: Background, Applications, Protocols, and More: A Guide to One of the Most Commonly Used Cell Lines, https://www.synthego.com/hek293, Nov. 5, 2021, 2:56PM, pp. 1-10.

* cited by examiner

SEQUENCE LISTING

<160> NUMBER OF SEQ ID NOS: 1

<210> SEQ ID NO 1
<211> LENGTH: 145
<212> TYPE: DNA
<213> ORGANISM: Adeno-associated virus

<400> SEQUENCE: 1

```
aggaacccct agtgatggag ttggccactc cctctctgcg cgctcgctcg ctcactgagg     60
ccgggcgacc aaaggtcgcc cgacgcccgg gctttgcccg ggcggcctca gtgagcgagc   120
gagcgcgcag agagggagtg gccaa                                         145
```

AAV VECTOR AND ASSAY FOR ANTI-AAV (ADENO-ASSOCIATED VIRUS) NEUTRALIZING ANTIBODIES

RELATED APPLICATION INFORMATION

This application is the National Phase of International Application No. PCT/US2014/046428, filed Jul. 11, 2014 which designated the U.S. and that International Application was published under PCT Article 21(2) in English, and claims priority to application Ser. No. 61/845,841, filed Jul. 12, 2013, all of which applications are expressly incorporated herein by reference in their entirety.

GOVERNMENT SUPPORT

This invention was made with government support under grant number HL078810 awarded by the National Institutes of Health. The government has certain rights in the invention.

SEQUENCE LISTING

The subject application contains a Sequence Listing which has been submitted electronically in ASCII format and is hereby incorporated by reference in its entirety. Said ASCII copy, created on Jan. 10, 2017, is named "USCHOP0444950_ST25.txt" and is 782 bytes in size.

INTRODUCTION

Humoral immunity against adeno-associated virus (AAV) vectors represents an important barrier to intravascular gene transfer, resulting in clearance of the vector before it enters the target cell. Antibodies directed against the AAV capsid are highly prevalent in humans, a natural host for this virus, and crossreact with a wide range of serotypes because of the degree of homology of capsid protein sequence. As a result, even relatively low titers of neutralizing antibodies (NAbs) can block AAV transduction when the vector is introduced into the bloodstream. Conversely, gene transfer to the eye, the brain or direct intramuscular delivery of AAV vectors seems to be less susceptible to neutralization by NAb.

NAbs to AAV are found in synovial fluid (SF) and have the potential to inhibit vector-mediated transduction in a serotype dependent manner. However, little is known about the Nab levels against different serotypes in the SF and the relationship between anti-AAV NAb titer in the serum vs SF. Finally, as NAb can efficiently block AAV-mediated transduction in vivo, strategies to overcome humoral immunity to the viral capsid are of great importance to achieve successful gene transfer.

SUMMARY

Disclosed herein are virus vectors, virus particles, and methods and uses of screening for, detecting, analyzing and determining amounts of virus antibody, or neutralizing antibody activity of samples. Such virus vectors, virus particles, and methods and uses are applicable to a broad range of virus types, such as lentiviruses, Adenovirus, and adeno-associated virus (AAV) serotypes. Using different virus vectors, virus particles, and antibody screening methods and uses, anti-virus immunoglobulins (g), such as IgG, IgA, IgM, IgE, IgD can screened for, detected, analyzed and amounts determined.

Results from this screening, detecting, analyzing or determining amounts can be used to determine suitability of a subject, or vector types or doses for gene therapy (to replace or supplement a defective or deficient gene or to knockdown or knockout expression of a defective or undesirable gene) using lentiviruses, adenovirus, and adeno-associated virus (AAV) serotypes. For example, if a subject expresses little or no antibody against a particular virus serotype, such as AAV serotype 2 (AAV2), then the subject would be a suitable candidate for AAV2 mediated gene therapy. If a subject expresses a moderate or substantial amount of antibody against a particular virus serotype, such as AAV2, then the subject may require a larger dose or more doses of AAV2 vector for AAV2 mediated gene therapy, or combined with agents or methods of pharmacological modulation of B-cell responses. Gene transfer in subjects can therefore be achieved who would otherwise not be ideal candidates for virus vector gene transfer therapies. Alternatively, if available a non-AAV2 vector (such as another AAV serotype) could be employed for gene therapy for such a subject. Accordingly, virus vector administration can be personalized, based upon the presence or absence, type and/or amount (e.g., titer) of virus antibodies that are present (if any), and a vector selected for a given subject based upon the presence, type and amount of virus antibody in the subject.

In accordance with the invention, there are provided recombinant AAV vector sequences, the vector sequences including a reporter transgene. In one embodiment, recombinant AAV vector sequence includes a reporter transgene, which reporter transgene includes (a) a single-stranded or a self-complementary genome, (b) is operably linked to one or more expression regulatory elements, and (c) is flanked by one or more flanking elements.

In accordance with the invention, there are also provided recombinant AAV vectors, in which the vector includes a reporter transgene. In one embodiment, recombinant AAV vector includes a reporter transgene, which reporter transgene includes (a) a single-stranded or a self-complementary genome, (b) is operably linked to one or more expression regulatory elements, and (c) is flanked by one or more flanking elements. In particular embodiments, the recombinant AAV vector comprises an infectious recombinant AAV particle.

In accordance with the invention, there are further provided methods and uses for analyzing for or detecting or measuring antibodies that bind to AAV. In one embodiment, a method or use includes: A) providing infectious recombinant AAV particles that encapsidate a recombinant vector, wherein (i) the vector includes a reporter transgene, (ii) the reporter transgene comprises a single-stranded or a self-complementary genome, and (iii) the reporter transgene is operably linked to one or more expression regulatory elements and flanked by one or more flanking elements; B) providing a biological sample from a subject for analyzing or detecting antibodies that bind to AAV; C) providing cells that can be infected with said infectious recombinant AAV particles; D) contacting or incubating the infectious recombinant AAV particles of (A) with the biological sample of (B) thereby producing a resulting mixture (M); contacting the cells of (C) with the resulting mixture (M) under conditions in which the infectious recombinant AAV particles of (A) can infect and express the reporter transgene in said cells; measuring expression of the reporter transgene; and comparing said reporter transgene expression of (f) to reporter transgene expression of a control, said control either (i) a negative (−) control lacking antibodies that bind to AAV, or (ii) having a predetermined amount of antibodies that bind to AAV. A reporter transgene expression of (f) greater than reporter transgene expression of said (−) control analyzes for or detects or measures presence of antibodies that bind to AAV in the biological sample. A reporter transgene expression of (f) compared to reporter transgene expression of the predetermined amount of antibodies that bind to AAV analyzes, or detects or measures antibodies in the biological sample that are greater or less than the control.

In particular aspects of the invention, the recombinant vector comprises an AAV vector. In more particular aspects, the AAV vector comprises an AAV1, AAV2, AAV3, AAV4, AAV5, AAV6, AAV7, AAV8, AAV9, AAV10, AAV11, AAV12, Rh74, or Rh10 vector, or a hybrid or chimera of any of the foregoing AAV vectors.

In particular aspects of the invention, the method or use is performed in vitro. For example, cells may be contacted or incubated in vitro with infectious recombinant AAV particles.

In various embodiments of the invention, antibodies analyzed, detected or measured bind to a viral envelope or capsid protein, such as an AAV capsid protein. In particular aspects of the invention, antibodies analyzed, detected or measured bind to AAV serotype AAV1, AAV2, AAV3, AAV4, AAV5, AAV6, AAV7, AAV8, AAV9, AAV10, AAV11, AAV12, Rh74, or Rh10, or a hybrid or chimera of any of the foregoing AAV serotypes.

In various embodiments of the invention, the predetermined amount of antibodies that bind to AAV can be any AAV serotype. In particular aspects of the invention, the predetermined amount of antibodies bind to AAV1, AAV2, AAV3, AAV4, AAV5, AAV6, AAV7, AAV8, AAV9, AAV10, AAV11, AAV12, Rh74, or Rh10, or a hybrid or chimera of any of the foregoing AAV serotypes.

In further particular aspects of the invention, cells include mammalian cells such as primate (e.g., human) cells. In more particular aspects of the invention, cells include HEK-293 (e.g., 2V6.11) cells, CHO, BHK, MDCK, 10T1/2, WEHI cells, COS, BSC 1, BSC 40, BMT 10, VERO, W138, MRC5, A549, HT1080, 293, B-50, 3T3, NIH3T3, HepG2, Saos-2, Huh7, HER, HEK, HEL, or HeLa cells.

In additional aspects, cells provide nucleic acid sequences encoding helper functions for AAV replication and/or genomic integration. In more particular aspects of the invention, cells express adenovirus E4 gene, and or AAV rep or cap.

In further aspects, the cells can be infected with AAV particles comprising a VP1, VP2 or VP3 sequence 90% or more identical to a VP1, VP2 or VP3 sequence of AAV serotype AAV1, AAV2, AAV3, AAV4, AAV5, AAV6, AAV7, AAV8, AAV9, AAV10, AAV11, AAV12, Rh74, or Rh10, or a hybrid or chimera of any of the foregoing AAV serotypes, or the cells can be infected with AAV serotype AAV1, AAV2, AAV3, AAV4, AAV5, AAV6, AAV7, AAV8, AAV9, AAV10, AAV11, AAV12, Rh74, or Rh10, or a hybrid or chimera of any of the foregoing AAV serotypes.

In still further aspects, the cells are contacted with the resulting mixture (M) for a period of 6-48 hours, for a period of 12-36 hours, for a period of 20-30 hours, or for a period of about 24 hours. In yet further aspects, the cells are lysed prior to measuring expression of the reporter transgene.

In various embodiments of the invention, a reporter transgene encodes a protein that provides an enzymatic, colorimetric, fluorescent, luminescent, chemiluminescent, or electrochemical signal. In particular aspects, a reporter transgene comprises a luciferase gene, such as a renilla luciferase or a firefly luciferase gene. In further particular aspects, a reporter transgene comprises a β-galactosidase gene, a β-glucoronidase gene, a chloramphenicol transferase gene. In further particular aspects, a reporter transgene encodes a green fluorescent protein (GFP), a red fluorescent protein (RFP) or an alkaline phosphatase.

In further various embodiments of the invention, a reporter transgene is a single stranded genome, or a reporter transgene is a self-complementary genome. In additional aspects of the invention, a self-complementary reporter transgene genome comprises a double strand (or duplex) inverted repeat sequence structure. In further aspects of the invention, a self-complementary reporter transgene genome comprises a hairpin loop structure.

In further embodiments of the invention, a vector or vector sequence includes one (or more) expression regulatory elements, such as a promoter and/or enhancer nucleic acid sequence operable in mammalian cells. In still further embodiments of the invention, a vector or vector sequence includes one or more flanking element(s), such as one or more AAV inverted terminal repeat sequences (ITRs). In further aspects of the invention, a reporter transgene is positioned between the one or more flanking element(s), such as one or more 5' and/or 3' AAV ITRs.

In more particular embodiments of the invention, a vector or vector sequence includes a first inverted terminal repeat (ITR) of an AAV; a promoter operable in mammalian cells; the reporter transgene; a polyadenylation signal; and optionally a second ITR of an AAV. In particular aspects of the invention, a recombinant vector or vector sequence includes a restriction site to allow insertion of the reporter transgene downstream of a promoter operable in mammalian cells, and a posttranscriptional regulatory element downstream of the restriction site. In further particular aspects of the invention, a recombinant vector or vector sequence includes a restriction site to allow insertion of the reporter transgene downstream of a promoter operable in mammalian cells, and a posttranscriptional regulatory element downstream of the restriction site. In particular aspects, the promoter, the restriction site and the posttranscription regulatory element are located downstream of a 5' AAV ITR and upstream of an optional 3' AAV ITR.

In more particular aspects of the invention, a flanking element(s) is a mutated or variant AAV ITR that is not processed by AAV Rep protein. In additional more particular aspects of the invention, a flanking element(s) is a mutated or variant AAV ITR that allows or facilitates formation of the self-complementary reporter transgene genome into a double strand inverted repeat sequence structure in the infectious recombinant AAV particle. In further more particular aspects of the invention, a flanking element(s) is a mutated or variant AAV ITR with a deleted D sequence and/or a deleted terminal resolution site (TRS) sequence (e.g., a mutated or variant AAV ITR is positioned between the self-complementary sequences of the reporter transgene). In still further more particular aspects of the invention, a mutated or variant AAV ITR comprises an AAV2 ITR having one or more nucleotides corresponding to nucleotides 122-144 of AAV2 genome sequence mutated, modified, varied or deleted.

In further particular embodiments of the invention, infectious recombinant AAV particles comprise an AAV serotype that infects primates. In particular aspects, infectious recombinant AAV particles comprise an AAV serotype that infects humans or rhesus macaques. In various particular aspects, infectious recombinant AAV particles comprise a VP1, VP2 or VP3 sequence 90% or more identical to a VP1, VP2 or VP3 sequence of AAV serotype AAV1, AAV2, AAV3, AAV4, AAV5, AAV6, AAV7, AAV8, AAV9, AAV10, AAV11, AAV12, Rh74, or Rh10, or a hybrid or chimera of any of the foregoing AAV serotypes. In further various particular aspects, infectious recombinant AAV particles comprise AAV serotype AAV1, AAV2, AAV3, AAV4, AAV5, AAV6, AAV7, AAV8, AAV9, AAV10, AAV11, AAV12, Rh74, or Rh10, or a hybrid or chimera of any of the foregoing AAV serotypes.

In various embodiments of the invention, a biological sample comprises a primate sample. Such samples include without limitation, serum, plasma, or blood, such as human serum, human plasma or human blood.

In further embodiments of the invention, a biological sample is or has been heat inactivated. In particular aspect, a biological sample is or has been heat inactivated at about 50-70 degrees Celsius for a period of about 15 minutes up to one hour, or is or has been heat inactivated at about 56 degrees Celsius for a period of about 30 minutes.

In still further embodiments of the invention, a biological sample is diluted prior to contact or incubating with infectious recombinant AAV particles. In particular aspects, a plurality of dilutions of the biological sample is analyzed, measured or detected. In further particular aspects, a plurality of different dilution ratios of the biological sample are analyzed, measured or detected. In more particular aspects, a biological sample is diluted between 1:1 and 1:500 prior to contacting or incubating with the infectious recombinant AAV particles; or a biological sample is diluted between 1:500 and 1:5000 prior to contacting or incubating with the infectious recombinant AAV particles. In additional particular aspects, at least 2, 3, 4, 5 or 6 different dilution ratios of the biological sample are analyzed, measured or detected.

In various embodiments of the invention, a subject (e.g., a candidate for viral vector mediated gene therapy, such as AAV vector) subject is a mammal (e.g., a primate). In a particular aspect, a subject is a human.

In various embodiments of the invention, a subject suffers from a disorder due to insufficient expression or activity of a protein, or suffers from a disorder due to expression or activity of an abnormal, aberrant or undesirable protein.

In further various embodiments of the invention, a subject suffers from a genetic disorder. In additional various embodiments of the invention, a subject is a candidate for gene replacement or supplement therapy, such as a gene knockdown or knockout therapy. In more particular embodiments of the invention, a subject suffers from a lung disease (e.g., cystic fibrosis), a bleeding disorder (e.g., hemophilia A or hemophilia B with or without inhibitors), thalassemia, a blood disorder (e.g., anemia), Alzheimer's disease, Parkinson's disease, Huntington's disease, amyotrophic lateral sclerosis (ALS), epilepsy, lysosomal storage diseases, a copper or iron accumulation disorders (e.g., Wilson's or Menkes disease) lysosomal acid lipase deficiency, a neurological or neurodegenerative disorder, cancer, type 1 or type 2 diabetes, Gaucher's disease, Hurler's disease, adenosine deaminase deficiency, a metabolic defect (e.g., glycogen storage diseases), a retinal degenerative disease (such as RPE65 deficiency, choroideremia, and other diseases of the eye), a disease of solid organs (e.g., brain, liver, kidney, heart), or an infectious viral (e.g., hepatitis B and C, HIV, etc.), bacterial or fungal disease.

In various further embodiments of the invention, the amount of antibodies that bind to AAV in the biological sample is determined/calculated. In one embodiment, antibodies are calculated based upon the reporter transgene expression of (f) compared to negative (−) control. In another embodiment, antibodies are calculated based upon the reporter transgene expression of (f) compared to the predetermined amount of AAV antibodies control.

In still further embodiments of the invention, the amount of antibodies is entered into a database or a report associated with the subject from which the biological sample was obtained. The entry thereby produces a database entry or report associated with the subject.

DETAILED DESCRIPTION

Figure 1A:
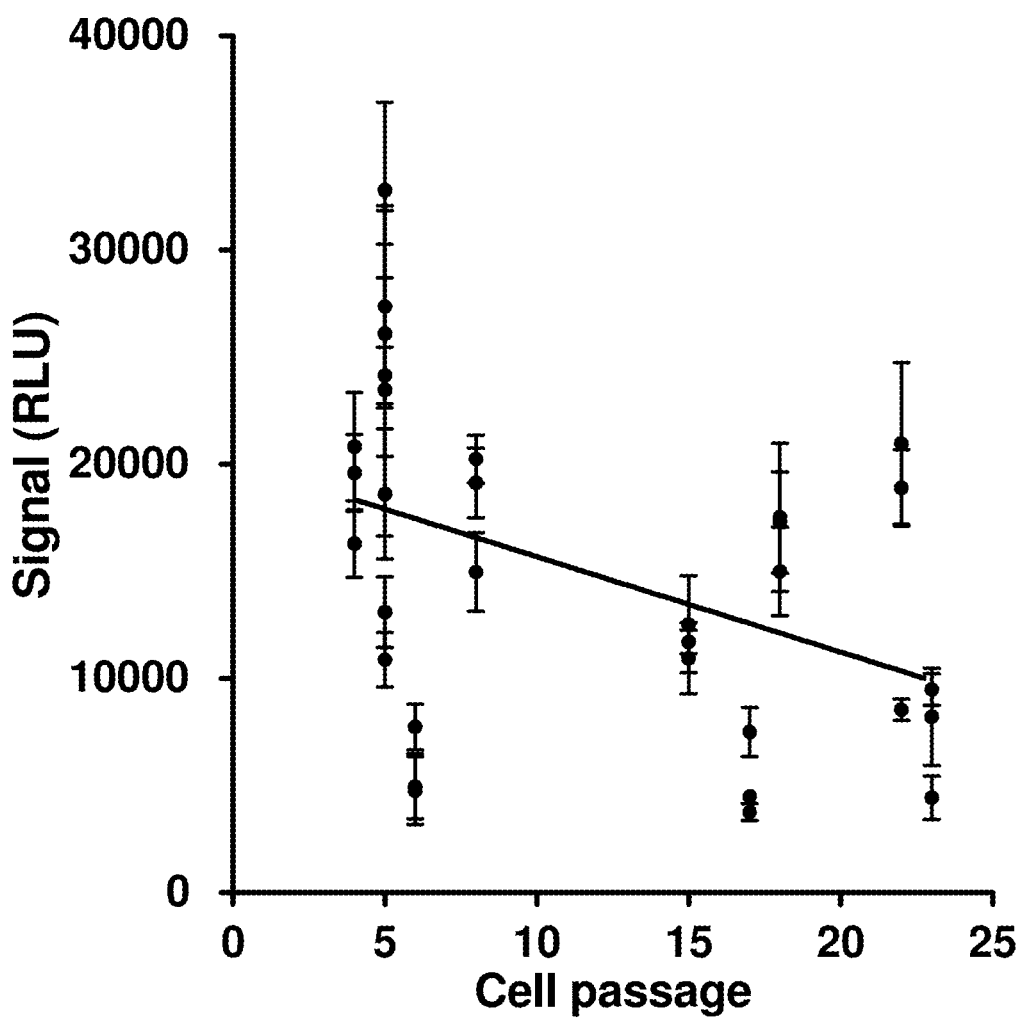
FIG. 1A shows luciferase reporter gene Max Signal as a function of number of cell passages. Statistical analysis performed using GraphPad Prism Version 5.0b. Linear regression: R2 curve 0.1509, p<0.0001, the slope of the curve is significantly non-zero. Additional statistical analysis was performed by comparing the mean of Max Signal (RLU) obtained with cells from passages 1-12 with that of passages 13-25. For this purpose, a two-tailed unpaired t test was used. Mean+/−standard error of the mean: passage 1-12, 17921+/−1181, n=53; passage 13-25, 11427+/−903, n=45, p<0.0001.

The invention is based, at least in part, on a sensitive assay for screening for, detecting, analyzing and determining amounts of virus antibody, or neutralizing antibody. The invention therefore provides vectors, virus vectors and particles, and methods and uses of screening for, detecting, analyzing and determining amounts of virus antibody, or neutralizing antibody, for example, in a sample.

As set forth herein, vector sequences, vectors (e.g., virus vectors) and particles provide a means of screening for, detecting, analyzing and determining amounts of virus antibody, or neutralizing antibody. Invention vector sequences, vectors (e.g., virus vectors) and particles, and methods and uses of screening for, detecting, analyzing and determining amounts of virus antibody employ a reporter transgene (the transgene provides a detectable signal), which transgene comprises a single-stranded or a self-complementary genome. A self-complementary transgene genome becomes double stranded or is a double stranded dimer, when packaged into a virus particle (virus vector) or upon virus vector cell transduction and virus uncoating within the transduced cell.

The terms "complementary" or "complement" when used in reference to a polynucleotide or nucleic acid molecule, such as a transgene, refers to a plurality of chemical bases such that through base pairing one single stranded sequence does or is capable of "specifically hybridizing" or binding (annealing) to another single stranded sequence to form a double-strand or duplex molecule. The ability of two single stranded sequences to specifically hybridize or bind (anneal) to each other and form a double-stranded (or duplex) molecule is by virtue of the functional group of a base on one strand (e.g., sense), which will hydrogen bond to another base on an opposing nucleic acid strand (e.g., anti-sense). The complementary bases that are able to bind to each other typically are, in DNA, A with T and C with G, and, in RNA, C with G, and U with A. Thus, an example of a self complementary sequence could be ATCGXXXCGAT, the X represents non-complementary bases, and the structure of such a double-stranded or duplex molecule with the X bases not hybridizing would appear as:

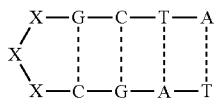

The terms "complementary" and "complement" when used in reference to a polynucleotide or nucleic acid molecule, such as a transgene, is therefore intended to describe a physical state in which a double-stranded or duplex polynucleotide or nucleic acid molecule forms, or simply describes a sequence relationship between two polynucleotide or nucleic acid molecules such that each single strand molecule could form a double strand with the other. "Complementary" and "complement" therefore refers to the relationship of bases of each polynucleotide or nucleic acid molecule strand, and not that the two-strands must exist as a double stranded (or duplex) configuration or physical state with each other in a duplex.

Typically for viral vectors that package single stranded nucleic acid, such as AAV, the inverted terminal repeat (ITR) sequences participate in replication and form a hairpin loop, which contributes to so self-priming that allows initiation and synthesis of the second DNA strand. After synthesis of the second DNA strand, an AAV ITR has a so-called terminal resolution site (TRS), such that the hairpin loop is cleaved into two single strands each with a 5' and 3' terminal repeat for virus packaging.

Use of a deleted, mutated, modified, or non-functional TRS in at least one ITR results in formation of a double strand duplex that is not cleaved at the TRS. In the embodiment of a self-complementary reporter transgene double-stranded duplex structure, there is typically an ITR with a deleted, mutated or variant TRS located between the two complementary strands. The non-cleavable or non-resolvable TRS allows for self-complementary reporter transgene double-stranded duplex structure formation since the double strand form is not cleaved. Either the non-resolvable ITR with deleted, mutated or variant TRS, or resolvable ITR, may be suitable for virus packaging. Resolvable AAV ITR need not be a wild-type ITR sequence as long as the ITR mediates a desired function, e.g., virus packaging or integration.

The ITR and TRS sequences of various AAV serotypes that may be deleted, mutated, modified, or varied include any AAV serotype set forth herein or that would be known to the skilled artisan. For example, ITR and TRS sequences of various AAV serotypes include AAV-1, -2, -3, -4, -5, -6, -7, -8, -9, -10, -11, -rh74, -rh10 or AAV-2i8, for example. For AAV2, a representative mutated TRS sequence is: "CGGTTG."

For a vector or vector sequence with a self-complementary reporter transgene sequences considered outside of the transgene, such as one or more ITRs, expression or regulatory control sequences, downstream sequences, etc., such sequences of the vector sequence outside of the reporter transgene can, but need not be self-complementary. Self-complementary can therefore be used in a specific context, for example, in reference to a transgene, such as a reporter transgene, such that only the transgene, such as the reporter transgene is self-complementary, whereas the other non-transgene sequences may or may not be self-complementary.

For a self-complementary transgene, not all bases in a single strand must be complementary to each and every base of the opposing complementary strand. There need only be a sufficient number of complementary nucleotide or nucleoside bases to enable the two polynucleotide or nucleic acid molecules to be able to specifically hybridize or bind (anneal) to each other. Hence, there may be short sequence segments or regions of non-complementary bases between the self-complementary polynucleotide or nucleic acid molecules. For example, 1-5, 5-10, 10-20, 20-30, 30-40, 40-50, 50-75, 75-100, or 100-150 or more contiguous or non-contiguous non-complementary bases may be present but there may be sufficient complementary bases over the lengths of the two sequences such that the two polynucleotide or nucleic acid molecules are able to specifically hybridize or bind (anneal) to each other and form a double-strand (or duplex) sequence. Accordingly, sequences of the two single stranded regions may be less than 100% complementary to each other and yet still be able to form a double-strand duplex molecule. In particular embodiments, two single strand sequences have at least 70%, at least 75%, at least 80%, at least 85%, at least 90%, at least 95%, at least 98%, at least 99% or more complementarity to each other.

Such segments or regions of non-complementary bases between the self-complementary polynucleotide or nucleic acid molecules can be internal sequences, such that when the complementary portions of the two single stranded molecules form a double strand or duplex, the non-complementary bases form a loop or bulge configuration, and the overall structure resembles a hairpin. Such segments or regions of non-complementary bases between the self-complementary polynucleotide or nucleic acid molecules can also flank the complementary regions, in which case either or both if the 5' or 3 flanking regions may not form a double-strand duplex.

A self-complementary transgene which forms a double strand or duplex sequence typically is expressed faster (more rapid onset) than a single stranded transgene counterpart. Thus, such expression can be detected by measuring expression over time, such as at defined time points (e.g., 1, 2, 34, 5, 6, 7, 8, 9, 10, 11, 12, 12-16, 16-20, 20-24 hours, for example). Furthermore, the amount of expression of the double stranded self-complementary transgene typically is greater than a single stranded reporter transgene counterpart. Thus, such expression can be detected by measuring at a point in time in which expression would be considered to be approaching or at a maximum. Accordingly, a double stranded self-complementary transgene configuration enhances detection sensitivity and can improve accuracy of virus antibody quantity determinations, particularly of viruses which are less efficient at infecting particular cell types, i.e., viruses which have relatively low rates of cell infectivity or tropism.

As used herein, a "vector" can refer to a viral particle, such as a parvovirus (e.g., AAV) that can be used to deliver nucleic acid (e.g., reporter transgene) into cells, and which vector includes nucleic acid (e.g., reporter transgene) packaged into virions or encapsidated by viral proteins (envelope proteins or capsid proteins, such as AAV capsid). Alternatively, the term "vector" may be used in a more limited context to refer to the vector sequence or nucleic acid. Thus, a vector as used herein can be used to refer to a virus particle that includes nucleic acid (e.g., reporter transgene), or to refer to only a nucleic acid or sequence, which sequence can be referred to as a "vector sequence" or the like.

A viral vector is derived from or based upon one or more nucleic acid elements that comprise a viral genome. Particular viral vectors include parvovirus vectors, such as adeno-associated virus (AAV) vectors.

In particular embodiments, a recombinant vector (e.g., AAV) is a parvovirus vector. Parvoviruses are small viruses with a single-stranded DNA genome. "Adeno-associated viruses" (AAV) are in the parvovirus family.

As used herein, the term "recombinant," as a modifier of vector, such as viral vectors, as well as a modifier of sequences such as recombinant polynucleotides and polypeptides, means that the compositions (e.g., AAV or sequences) have been manipulated (i.e., engineered) in a fashion that generally does not occur in nature. A particular example of a recombinant vector sequence, such as an AAV vector would be where a polynucleotide that is not normally present in the wild-type viral (e.g., AAV) genome is inserted within the viral genome. For example, an example of a recombinant vector would be where a heterologous polynucleotide (e.g., transgene) is cloned into the vector sequence, with or without 5', 3' and/or intron regions that the gene is normally associated within the vector such as a viral (e.g., AAV) vector genome. Although the term "recombinant" is not always used herein in reference to viral vectors, such as AAV vectors, as well as vector sequences and polynucleotides and polypeptides, recombinant forms of viral vectors such as AAV, vector sequences and polynucleotides and polypeptides, are expressly included in spite of any such omission.

A recombinant "vector" or "AAV vector" can be derived from the wild type genome of a virus, such as AAV by using molecular methods to remove the wild type genome from the virus (e.g., AAV) sequence, and replacing with a non-native nucleic acid, such as a reporter transgene. Typically, for AAV one or both inverted terminal repeat (ITR) sequences of the wild type AAV genome are retained in the AAV vector. A recombinant viral vector (e.g., AAV) is distinguished from a viral (e.g., AAV) genome, since all or a part of the viral genome sequence has been replaced with a non-native sequence with respect to the viral (e.g., AAV) nucleic acid such as a reporter transgene. Incorporation of a non-native sequence such as a reporter transgene therefore defines the viral vector (e.g., AAV) as a "recombinant" vector, which in the case of AAV can be referred to as an "rAAV vector."

A recombinant vector "genome" (e.g., a viral or an AAV vector genome) can be encapsidated or packaged into a virus (also referred to herein as a "particle" or "virion") for subsequent infection (transduction or transformation) of a cell, ex vivo, in vitro or in vivo. Where a recombinant AAV vector genome is encapsidated or packaged into an AAV particle, the particle can be referred to as a "rAAV." Such particles or virions will typically include proteins that encapsidate or package the vector genome. Particular examples include viral capsid and envelope proteins, and in the case of AAV, AAV capsid proteins.

For a recombinant plasmid, a vector "genome" refers to the portion of the recombinant plasmid sequence that is ultimately packaged or encapsidated to form a viral particle. In cases where recombinant plasmids are used to construct or manufacture recombinant vectors, the vector genome does not include the portion of the "plasmid" that does not correspond to the vector genome sequence of the recombinant plasmid. This non vector genome portion of the recombinant plasmid is referred to as the 'plasmid backbone,' which is important for cloning and amplification of the plasmid, a process that is needed for propagation and recombinant virus production, but is not itself packaged or encapsidated into virus (e.g., AAV) particles.

Thus, a vector "genome" refers to the portion of the vector plasmid that is packaged or encapsidated by virus (e.g., AAV), and which contains a heterologous (transgene) polynucleotide sequence. The non vector genome portion of the recombinant plasmid includes the backbone that is important for cloning and amplification of the plasmid, but is not itself packaged or encapsidated by virus (e.g., AAV).

Recombinant vector sequences are manipulated by insertion or incorporation of a polynucleotide. As disclosed herein, a vector sequence or plasmid generally contains at least an origin of replication for propagation in a cell and one or more expression control elements.

Recombinant vectors (e.g., AAV), vector sequences or plasmids, as well as methods and uses thereof, include any viral strain or serotype. As a non-limiting example, a recombinant vector (e.g., AAV) plasmid can be based upon any AAV genome, such as AAV-1, -2, -3, -4, -5, -6, -7, -8, -9, -10, -11, -rh74, -rh10 or AAV-2i8, for example. Such vectors can be based on the same of strain or serotype (or subgroup or variant), or be different from each other. As a non-limiting example, a recombinant vector (e.g., AAV) plasmid based upon one serotype genome can be identical to one or more of the capsid proteins that package the vector. In addition, a recombinant vector (e.g., AAV) plasmid can be based upon an AAV (e.g., AAV2) serotype genome distinct from one or more of the capsid proteins that package the vector. Thus, by way of illustration only, an rAAV-2 vector plasmid could have at least one (or more) of the three capsid proteins from AAV-2 or any other AAV capsid, such as AAV-1, -3, -4, -5, -6, -7, -8, -9, -10, -11, -rh74, -rh10 or AAV-2i8 capsid, for example.

As disclosed herein, the vector is used to transduce target cells with a reporter transgene, which transgene is subsequently transcribed and optionally translated thereby providing a detectable signal to detect or measure transgene expression. The amount of signal is proportional to the efficiency of cell transduction and subsequent expression. Antibodies that bind to vector proteins that package or encpasidate the reporter transgene will inhibit transgene transduction and subsequent expression. Thus, detection, measurement and analysis for the presence of antibodies that bind to vector proteins, such as viral (e.g., AAV) vector proteins can be ascertained.

In the assays described herein, the detection, measurement and analysis of antibodies will be determined by the identity of the envelope or capsid protein(s) that package or encapsidate the reporter transgene. Thus, if it is desired to detect AAV-2 antibodies, the reporter transgene should be encpasidated by AAV-2 capsid protein(s). If it is desired to detect AAV-7 antibodies, the reporter transgene should be encpasidated by AAV-7 capsid protein(s). If it is desired to detect AAV-8 antibodies, the reporter transgene should be encpasidated by AAV-8 capsid protein(s). If antibody is present, the antibody binds to the envelope or capsid protein(s) that encapsidates the reporter transgene, reducing cell transduction and consequent reporter transgene expression. The greater the amount of antibody that binds to envelope or capsid protein(s) the less vector transduction of cells and consequent reporter transgene expression.

Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

Recombinant vectors (e.g., AAV) and vector sequences, including AAV1, AAV2, AAV3, AAV4, AAV5, AAV6, AAV7, AAV8, AAV9, AAV10, AAV11, Rh10, Rh74 or AAV-2i8 can be constructed using recombinant techniques known to the skilled artisan, to include one or more heterologous polynucleotide sequences (transgenes) flanked with one or more functional AAV ITR sequences. Such vectors can have one or more of the wild type AAV genes deleted in whole or in part, for example, a rep and/or cap gene, but retain at least one functional flanking ITR sequence (e.g., AAV2 or any other AAV serotype ITR), as necessary for the rescue, replication, and packaging of the recombinant vector into an AAV vector particle. An AAV vector genome would therefore include sequences required in cis for replication and packaging (e.g., functional ITR sequences)

The terms "transgene," "sequence," "polynucleotide" and "nucleic acid" are used interchangeably herein to refer to all forms of nucleic acid, oligonucleotides, including deoxyribonucleic acid (DNA) and ribonucleic acid (RNA). Transgenes include genomic DNA, cDNA and antisense DNA, spliced or unspliced. Transgenes include naturally occurring, synthetic, and intentionally altered or modified polynucleotides as well as analogues and derivatives. Transgenes are typically single or double stranded, linear or circular, and can be of any length. In discussing transgenes, a sequence or structure of a particular polynucleotide may be described herein according to the convention of providing the sequence in the 5' to 3' direction.

A "heterologous" transgene, sequence, or polynucleotide refers to a polynucleotide inserted into a vector (e.g., AAV) for purposes of vector mediated transfer/delivery of the polynucleotide into a cell. Heterologous transgenes, sequences, or polynucleotides are typically distinct from vector (e.g., AAV) nucleic acid, i.e., are non-native with respect to viral (e.g., AAV) nucleic acid sequences. Once transferred/delivered into the cell, a heterologous transgene, sequence, or polynucleotide, contained within the virion, can be expressed (e.g., transcribed, and translated if appropriate). Alternatively, a transferred/delivered heterologous transgene, sequence, or polynucleotide in a cell, contained within the virion, need not be expressed. Although the term "heterologous" is not always used herein in reference to transgenes, sequences, or polynucleotides, reference to a transgene, sequence, or polynucleotide even in the absence of the modifier "heterologous" is intended to include heterologous transgenes, sequences, and polynucleotides in spite of the omission.

The term "transgene" is used herein to conveniently refer to a heterologous polynucleotide that has been introduced into a cell or organism. Transgenes include any polynucleotide, such as a gene that is transcribed into a polynucleotide, or a gene that encodes a polypeptide or protein typically by way of an intermediate transcript.

As used herein, a "reporter" transgene is a gene that provides a detectable signal. The signal may be provided by the transgene itself, a transcript of the transgene or a protein encoded by the transgene. Particular non-limiting examples of reporter transgenes include luciferase gene which encodes luciferase protein, etc.

The "polypeptides," "proteins" and "peptides" encoded by the "transgene" or "polynucleotide sequences," include full-length native sequences, as with naturally occurring proteins, as well as functional subsequences, modified forms or sequence variants so long as the subsequence, modified form or variant retains some degree of functionality of the native full-length protein. In methods and uses of the invention, such polypeptides, proteins and peptides encoded by the transgene or polynucleotide sequences can be but are not required to be identical to the wild type protein.

All mammalian and non-mammalian forms of transgene, sequence and polynucleotides including the non-limiting reporter transgenes and encoded proteins disclosed herein are expressly included, either known or unknown. Thus, the invention includes reporter transgenes and proteins from non-mammals, mammals other than humans, and humans, which reporter transgenes and proteins are detectable in cells after transduction or transfer as described herein.

In a cell having a transgene, the transgene has been introduced/transferred by way of vector, such as viral vector (e.g., AAV). This process is referred to as "transduction" or "transformation" or "transfection" of the cell. The terms "transduce," "transform," and "transfect" refers to introduction of a molecule such as a transgene into a cell.

A cell into which the transgene has been introduced is referred to as a "transformed cell" or "transformant." Accordingly, a "transduced," "transformed" or "transfected" cell (e.g., in a mammal, such as a cell or tissue or organ cell), means a genetic change in a cell following incorporation of an exogenous molecule, for example, a polynucleotide or protein (e.g., a transgene) into the cell. Thus, a "transduced," "transfected" or "transformed" cell is a cell into which, or a progeny thereof in which an exogenous molecule has been introduced, for example. The cell(s) can be propagated and the introduced transgene transcribed and/or protein expressed.

The introduced transgene may or may not be integrated into nucleic acid of the recipient cell. If an introduced transgene becomes integrated into the nucleic acid (genomic DNA) of the recipient cell or organism it can be stably maintained in that cell or organism and further passed on to or inherited by progeny cells or organisms of the recipient cell or organism. Finally, the introduced transgene may exist in the recipient cell or host organism only transiently.

Cells that may be a target for transduction with a vector (e.g., viral vector) bearing transgene may be any cell susceptible to infection with the vector. Such cells may have low, moderate or high rates of susceptibility to infection. Accordingly, target cells include a cell of any tissue or organ type, of any origin (e.g., mesoderm, ectoderm or endoderm). Particular non-limiting examples of cells include liver (e.g., hepatocytes, sinusoidal endothelial cells), pancreas (e.g., beta islet cells), lung, central or peripheral nervous system, such as brain (e.g., neural, glial or ependymal cells) or spine, kidney (HEK-293 cells), eye (e.g., retinal, cell components), spleen, skin, thymus, testes, lung, diaphragm, heart (cardiac), muscle or psoas, or gut (e.g., endocrine), adipose tissue (white, brown or beige), muscle (e.g., fibroblasts), synoviocytes, chondrocytes, osteoclasts, epithelial cells, endothelial cells, salivary gland cells, inner ear nervous cells or hematopoietic (e.g., blood or lymph) cells. Additional examples include stem cells, such as pluripotent or multipotent progenitor cells that develop or differentiate into liver (e.g., hepatocytes, sinusoidal endothelial cells), pancreas (e.g., beta islet cells), lung, central or peripheral nervous system, such as brain (e.g., neural, glial or ependymal cells) or spine, kidney, eye (retinal, cell components), spleen, skin, thymus, testes, lung, diaphragm, heart (cardiac), muscle or psoas, or gut (e.g., endocrine), adipose tissue (white, brown or beige), muscle (e.g., fibroblasts), synoviocytes, chondrocytes, osteoclasts, epithelial cells, endothelial cells, salivary gland cells, inner ear nervous cells or hematopoietic (e.g., blood or lymph) cells.

Viral vectors such as AAV vectors and vector sequences can include one or more "expression control elements" or "regulatory elements." Typically, expression control or regulatory elements are nucleic acid sequence(s) that influence expression of an operably linked polynucleotide. Control elements, including expression control and regulatory elements as set forth herein such as promoters and enhancers, present within a vector are included to facilitate proper heterologous polynucleotide (transgene) transcription and if appropriate translation (e.g., a promoter, enhancer, splicing signal for introns, maintenance of the correct reading frame of the gene to permit in-frame translation of mRNA and, stop codons etc.). Such elements typically act in cis but may also act in trans.

Expression control can be effected at the level of transcription, translation, splicing, message stability, etc. Typically, an expression control element that modulates transcription is juxtaposed near the 5' end of the transcribed polynucleotide (i.e., "upstream"). Expression control elements can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, 5000 to 10,000 or more nucleotides from the polynucleotide), even at considerable distances. Nevertheless, owing to the polynucleotide length limitations, for AAV vectors, such expression control elements will typically be within 1 to 1000 nucleotides from the polynucleotide.

Functionally, expression of operably linked heterologous polynucleotide (transgene) is at least in part controllable by the element (e.g., promoter) such that the element modulates transcription of the polynucleotide and, as appropriate, translation of the transcript. A specific example of an expression control element is a promoter, which is usually located 5' of the transcribed sequence. Another example of an expression control element is an enhancer, which can be located 5', 3' of the transcribed sequence, or within the transcribed sequence.

A "promoter" as used herein can refer to a DNA sequence that is located adjacent to a transgene. A promoter is typically operatively linked to an adjacent sequence, e.g., heterologous polynucleotide (transgene). A promoter typically increases an amount expressed from a heterologous polynucleotide (transgene) compared to an amount expressed when no promoter exists.

An "enhancer" as used herein can refer to a sequence that is located adjacent to the heterologous polynucleotide (transgene). Enhancer elements are typically located upstream of a promoter element but also function and can be located downstream of or within a DNA sequence (e.g., a transgene). Hence, an enhancer element can be located 100 base pairs, 200 base pairs, or 300 or more base pairs upstream or downstream of a heterologous polynucleotide (transgene). Enhancer elements typically increase expressed of a heterologous polynucleotide (transgene) above increased expression afforded by a promoter element.

Expression control elements (e.g., promoters) include those active in a particular tissue or cell type, referred to herein as a "tissue-specific expression control elements/promoters." Tissue-specific expression control elements are typically active in specific cell or tissue (e.g., liver, brain, central nervous system, spinal cord, eye, retina, bone, muscle, lung, pancreas, heart, kidney cell, etc.). Expression control elements are typically active in these cells, tissues or organs because they are recognized by transcriptional activator proteins, or other regulators of transcription, that are unique to a specific cell, tissue or organ type.

Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements that are not present in nature (see, e.g., Boshart et al, Cell, 41:521-530 (1985)), the SV40 promoter, the dihydrofolate reductase (DHFR) promoter, the chicken β-actin (CBA) promoter, the phosphoglycerol kinase (PGK) promoter and the elongation factor-1 alpha (EF1-alpha) promoter.

Expression control elements also can confer expression in a manner that is regulatable, that is, a signal or stimuli increases or decreases expression of the operably linked heterologous polynucleotide (transgene). A regulatable element that increases expression of the operably linked polynucleotide in response to a signal or stimuli is also referred to as an "inducible element" (i.e., is induced by a signal). Particular examples include, but are not limited to, a hormone (e.g., steroid) inducible promoter. A regulatable element that decreases expression of the operably linked polynucleotide in response to a signal or stimuli is referred to as a "repressible element" (i.e., the signal decreases expression such that when the signal, is removed or absent, expression is increased). Typically, the amount of increase or decrease conferred by such elements is proportional to the amount of signal or stimuli present; the greater the amount of signal or stimuli, the greater the increase or decrease in expression. Particular non-limiting examples include zinc-inducible sheep metallothionine (MT) promoter; the steroid hormone-inducible mouse mammary tumor virus (MMTV) promoter; the T7 polymerase promoter system (WO 98/10088); the tetracycline-repressible system (Gossen, et al., *Proc. Natl. Acad. Sci. USA,* 89:5547-5551 (1992)); the tetracycline-inducible system (Gossen, et al., *Science.* 268:1766-1769 (1995); see also Harvey, et al., *Curr. Opin. Chem. Biol.* 2:512-518 (1998)); the RU486-inducible system (Wang, et al., *Nat. Biotech.* 15:239-243 (1997) and Wang, et al., *Gene Ther.* 4:432-441 (1997)]; and the rapamycin-inducible system (Magari, et al., *J. Clin. Invest.* 100:2865-2872 (1997); Rivera, et al., Nat. Medicine. 2:1028-1032 (1996)). Other regulatable control elements which may be useful in this context are those which are regulated by a specific physiological state, e.g., temperature, acute phase.

Expression control elements also include the native elements(s) for the heterologous polynucleotide (transgene). A native control element (e.g., promoter) may be used when it is desired that expression of the heterologous polynucleotide should mimic the native expression. The native element may be used when expression of the heterologous polynucleotide is to be regulated temporally or developmentally, or in a tissue-specific manner, or in response to specific transcriptional stimuli. Other native expression control elements, such as introns, polyadenylation sites or Kozak consensus sequences may also be used.

As used herein, the term "operable linkage" or "operably linked" refers to a physical or functional juxtaposition of the components so described as to permit them to function in their intended manner. In the example of an expression control element in operable linkage with a transgene, the relationship is such that the control element modulates expression of the transgene. More specifically, for example, two DNA sequences operably linked means that the two DNAs are arranged (cis or trans) in such a relationship that at least one of the DNA sequences is able to exert a physiological effect upon the other sequence.

As disclosed herein, vectors including viral vectors such as AAV and vector sequences can include still additional nucleic acid elements. These elements include, without limitation one or more copies of an AAV ITR sequence, a promoter/enhancer element, a transcription termination signal, 5' or 3' untranslated regions (e.g., polyadenylation sequences) which flank a transgene, or all or a portion of intron 1. Such elements also optionally include a transcription termination signal. A particular non-limiting example of a transcription termination signal is the SV40 transcription termination signal.

The term "flank" as used herein in reference to elements of a vector or vector sequence, such as a transgene, means that the referenced element is positioned 5' or 3'. Thus, where an expression control element flanks a transgene, the control element is located 5' or 3' of the transgene. The term "flank" does not exclude intermediate sequences between them. For example, there may be an intervening sequence between the transgene and control element, for example, a restriction site. The restriction site may be an intervening sequence between the transgene and control element. Thus, a sequence that "flanks" an element indicates that one element is located 5' or 3' of the sequence but there may be an intervening sequence such that the flanking sequence is not immediately adjacent to the sequence that it flanks.

As disclosed herein, AAV vectors typically accept inserts of DNA having a defined size range which is generally about 4 kb to about 5.2 kb, or slightly more. Thus, when a reporter transgene is a single strand genome or is self-complementary, the transgene size will be less than about 4 kb to about 5.2 kb.

For shorter vector sequences, inclusion of a stuffer or filler in the insert fragment in order to adjust the length to near or at the normal size of the virus genomic sequence acceptable for AAV vector packaging into virus particle. In various embodiments, a filler/stuffer nucleic acid sequence is an untranslated (non-protein encoding) segment of nucleic acid. In particular embodiments of an AAV vector, a heterologous polynucleotide sequence has a length less than 4.7 Kb and the filler or stuffer polynucleotide sequence has a length that when combined (e.g., inserted into a vector) with the transgene sequence has a total length between about 3.0-5.5 Kb, or between about 4.0-5.0 Kb, or between about 4.3-4.8 Kb.

Polynucleotides and polypeptides including modified forms can be made using various standard cloning, recombinant DNA technology, via cell expression or in vitro translation and chemical synthesis techniques. Purity of polynucleotides can be determined through sequencing, gel electrophoresis and the like. For example, nucleic acids can be isolated using hybridization or computer-based database screening techniques. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

Polynucleotides and polypeptides including modified forms can also be produced by chemical synthesis using methods to the skilled artisan, for example, an automated synthesis apparatus (see, e.g., Applied Biosystems, Foster City, Calif.). Peptides can be synthesized, whole or in part, using chemical methods (see, e.g., Caruthers (1980). *Nucleic Acids Res. Symp. Ser.* 215; Horn (1980); and Banga, A. K., *Therapeutic Peptides and Proteins, Formulation, Processing and Delivery Systems* (1995) Technomic Publishing Co., Lancaster, Pa.). Peptide synthesis can be performed using various solid phase techniques (see, e.g., Roberge *Science* 269:202 (1995); Merrifield, Methods Enzymol. 289:3 (1997)) and automated synthesis may be achieved, e.g., using the ABI 431A Peptide Synthesizer (Perkin Elmer) in accordance with the manufacturer's instructions.

The term "isolated," when used as a modifier of a composition (e.g., vector), means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane. The term "isolated" does not exclude combinations produced by the hand of man, for example, a recombinant viral vector (e.g., AAV), vector sequence, or virus particle (e.g., AAV) that packages or encapsidates a vector genome and a pharmaceutical formulation. The term "isolated" also does not exclude alternative physical forms of the composition, such as hybrids/chimeras, multimers/oligomers, modifications (e.g., phosphorylation, glycosylation, lipidation) or derivatized forms, or forms expressed in host cells produced by the hand of man.

Reporter transgene bearing recombinant vectors, vector sequences, particles, etc., allow for analyzing for or detecting (measuring/quantifying) antibodies that bind to virus antigens, such as envelope or capsid proteins, including AAV capsids. In accordance with the invention, there are provided methods for analyzing for or detecting (measuring/quantifying) antibodies that bind to virus antigens. In one embodiment, a method includes providing infectious recombinant virus particles that encapsidate a recombinant vector, where (i) the vector includes a reporter transgene, (ii) the reporter transgene is a single-stranded or a self-complementary genome, and (iii) the reporter transgene is operably linked to one or more expression regulatory elements and flanked by one or more flanking elements; providing a biological sample from a subject for analyzing or detecting antibodies that bind to virus; providing cells that can be infected with said infectious virus particles; contacting or incubating the infectious recombinant virus particles with the biological sample thereby producing a resulting mixture; contacting the cells which can be infected with the resulting mixture under conditions in which the infectious recombinant virus particles can infect and express the reporter transgene in the cells; and measuring expression of the reporter transgene. Comparing the reporter transgene expression of the mixture to reporter transgene in a negative (−) control, where the (−) control either (i) lacks antibodies that bind to the infectious virus, or (ii) has a predetermined amount of antibodies that bind to the infectious virus. If reporter transgene expression of the mixture is greater than the (−) control this determines or detects the presence of antibodies that bind to virus in the biological sample.

In particular aspects, antibodies analyzed or detected bind to AAV particles, and/or the infectious recombinant virus particles comprise one or more AAV capsid protein(s), and/or the recombinant vector comprises a viral vector, such as an AAV vector, optionally with one or more AAV ITRs.

The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects.

The invention provides kits with packaging material and one or more components therein. A kit typically includes a label or packaging insert including a description of the components or instructions for use in vitro, in vivo, or ex vivo, of the components therein. A kit can contain a collection of such components, e.g., a vector (e.g., AAV), vector sequence, genome or virus particle or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include instructions for the clinician or subject for using one or more of the kit components in a method, or use. Instructions can include instructions for practicing any of the methods and uses described herein.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

All of the features disclosed herein may be combined in any combination. Each feature disclosed in the specification may be replaced by an alternative feature serving a same, equivalent, or similar purpose. Thus, unless expressly stated otherwise, disclosed features (e.g., a recombinant vector (e.g., AAV), vector sequence, plasmid, genome, or transgene, or recombinant virus particle (e.g., AAV) are an example of a genus of equivalent or similar features.

As used herein, the singular forms "a", "and," and "the" include plural referents unless the context clearly indicates otherwise. Thus, for example, reference to "a polynucleotide" includes a plurality of such polynucleotides, reference to "a vector" includes a plurality of such vectors, "a vector sequence, plasmid or genome" includes a plurality of such vectors, and reference to "a virus" or "particle" includes a plurality of such virions/particles.

As used herein, all numerical values or numerical ranges include integers within such ranges and fractions of the values or the integers within ranges unless the context clearly indicates otherwise. Thus, to illustrate, reference to at least 80% complementarity or identity, includes 81%, 82%, 83%, 84%, 85%, 86%, 87%, 88%, 89%, 90%, 91%, etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to more than 1, includes 2, 3, 4, 5, 6, etc. and up.

As used herein, all numerical values or ranges include fractions of the values and integers within such ranges and fractions of the integers within such ranges unless the context clearly indicates otherwise. Thus, to illustrate, reference to a numerical range, such as a percentage range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges of 11-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed.

EXAMPLES

Example 1

This example outlines various studies which evaluate the performance of an anti-AAV neutralizing antibody (NAb) assay. Such an assay can be used to screen subjects prior to enrollment in AAV vector-mediated gene transfer studies, as well as monitoring the present or amount of an anti-AAV neutralizing antibody during AAV vector-mediated gene transfer therapy, and post-AAV vector-mediated gene transfer therapy.

A substantial portion of the adult population has been exposed to wild-type AAV, typically through infection of the respiratory tract during childhood (Calcedo, 2011). Many people thus carry NAb to AAV that cross-react with the vector. An earlier clinical study (Manno et al. 2006) demonstrated that even a modest titer of NAb appears to block transduction when vector is delivered via the circulation. Other studies in non-human primates demonstrated that NAb titers as low as 1:5 completely block transduction of liver when vector is delivered through the circulation (Jiang et al., Blood 2006; Scallan, Blood 2006). The purpose of this assay is to determine NAb titer in subjects who present for inclusion in this study; those with pre-existing titers of >1:5 are not candidates for participation in the study.

This study employs a cell-based assay using an AAV vector expressing a reporter gene. Test serum is mixed with vector and the level of luciferase expression is compared to the level in a control sample not exposed to serum. The neutralizing titer is defined as the highest dilution of serum that results in 50% or greater inhibition of reporter gene (e.g., luciferase) expression as compared to wells with cells and vector but no serum but is reported in this document as a range; for example, if 50% or greater inhibition is observed at the 1:3.1 dilution of the sample, the titer is reported as a range of 1:3.1 to 1:10.

Three variables may affect assay precision and accuracy. They are the effect of cell passage number on assay result, operator variability and stability of results with freeze-thaw cycles of test serum and FACT. Serum samples for testing are normally received frozen on dry ice, stored at −80° C., and tested on the first thaw. Repeat assays may be conducted after an additional cycle of freeze-thaw.

Example 2

This example includes a description of certain materials and equipment used in studies described herein.

Materials: Test samples, subject source is serum or plasma (plasma must not contain heparin as anti-coagulant); PBS (phosphate buffered saline), sterile, Ca++ and Mg++ free, Invitrogen 14190-136 or equivalent; DMEM (Dulbecco's Modified Eagle Medium), Invitrogen 11965-084, or equivalent; FBS (fetal bovine serum), Hyclone SH30070.03IR, or equivalent; Penicillin/Streptomycin, Invitrogen 15140-122, or equivalent; L-Glutamine, 200 mM, Invitrogen 25030-156, or equivalent; cDMEM: complete DMEM (10% FBS, 1x Penicillin/Streptomycin, 1x L-Glutamine); Human Embryonic kidney cells stably expressing Ad-E4 (2V6.11 cells, ATCC Number: CRL-2784, below passage #26); Trypsin-EDTA (0.25% trypsin with EDTA 4Na) 1×, Invitrogen 25200-056, or equivalent; Density-gradient purified AAV-luciferase with capsid to vector genome (vg) ratio of 1, titered by dot-blot hybridization using luciferase plasmid as standard; Control FACT plasma, George King Biomedical Cat #0020-1, Lot number D9d1, stored frozen in 50 ul aliquots; Ponasterone A, Invitrogen H101-01, reconstituted in 100% ethanol at a concentration of 1 µg/mL; 500 mL Filtering system, 0.22 µm, Millipore SCGPU05RE; 96-well flat-bottomed tissue culture plate Corning 3595; Serological Pipettes, 5, 10, 25 mL; 50 mL centrifuge/conical tubes, Corning 430290; Reagent reservoirs, Costar 4870; 12-channel Multi-channel Pipettor 1-10 µl; 12-channel Multi-channel Pipettor 20-200 µl; P-20, P-200 and P-1000 Rainin Pipetman; Pipet Tips; Eppendorf tubes; 12-channel reservoirs, Costar 4877; Pipette Aid, Drummond 4-000-100 or equivalent; Vortex mixer; Trypan Blue (Sigma T8154 or equivalent) for viable cell counts; Renilla luciferase assay kit, Promega, catalog #E2820; Microsoft Excel software.

Equipment: Incubator at 37° C. and 5% $CO^2$; Biological Safety Cabinet; Hemacytometer, Reichert Bright-Line, Fisher #02-671-5, or equivalent; Inverted microscope; Freezer, −80° C.; Refrigerator, 2-8° C.; Incubator, 37° C.; Analytical balance; Veritas microplate luminometer, Turner Biosystems; and Shaker.

Example 3

This example includes a description of an exemplary method of detecting and/or quantifying anti-AAV antibodies.

2V6.11 cells (HEK-293 cells genetically modified to express the E4 gene from adenovirus) are transduced with AAV-luciferase vector alone, or vector mixed with serum in a range of dilutions. Twenty-four hours later, luciferase expression is detected using a luminometer. Cells are handled in an identical manner for these studies and for the routine assay.

The results run in triplicate are compared to the readings from vector alone (control) to determine the serum dilution at which luciferase expression is equal to or less than 50% of expression for vector alone. This assay uses luciferase reporter gene rather than lacZ as the reporter gene because it is more sensitive at low levels of inhibition.

Criteria to assess success of a run include:
1. Control plasma (pooled human plasma, FACT) yields a reading between 1:100 and 1:316 for AAV8 vectors and between 1:1000 and 1:3160 for AAV2 vectors.
2. Wells with cells but no vector and no serum give an acceptably low reading.
3. Wells with cells and vector but no serum give an acceptable reading.

For protocols in which vector is delivered through the circulation, a low (<1:5) or undetectable titer is typically preferred for inclusion in the study. For this reason, all results in this range are confirmed on a repeat run.

Inter-assay variability of the assay was estimated in a set of 9 human serum samples obtained from adults with severe hemophilia, resident in the U.S., with an anti-AAV8 NAb titer ranging from low-to-negative to high. The positive control FACT plasma (lot #D9d1) was included in these studies. FACT is a commercially available pool of normal human plasma samples from at least 30 human donors. Within the pooled population there will be individuals with high titer AAV antibodies, which would show up as positive in this assay. Use of plasma as a positive control is acceptable, as serum and plasma have similar levels of antibodies. One single lot of FACT plasma was used in the study.

In greater detail, reagents and samples are prepared: AAV-CBS-Renilla vector at a concentration >$2 \times 10^{11}$ vg/mL, and aliquots stored at −80° C. For Control plasma FACT, samples are heat-inactivated at 56° C. for 30 minutes and store aliquots at −80° C. For the test sample, samples (serum or plasma) are heat-inactivated at 56° C. for 30 minutes and aliquots stored at −80° C. For luciferase lysis and assay buffer, the reagents in Renilla Luciferase System are prepared and used according to the manufacturer. For diluent serum, fetal bovine serum is heat-inactivated at 56° C. for 30 minutes, and cooled to room temperature and filtered through a 0.22 μM filter. Aliquots are stored at −80° C.

In greater detail, for the procedure low passage (#2) 2V6.11 cells acquired through ATCC (cat. No. CRL-2784) are thawed in a 37° C. water bath for approximately two minutes, then washed twice with DMEM with 10% FBS, 1% Pen/Strep, and 1% glutamine. Cells are then plated in a T-75 cell culture flask, cultured for 2 days, trypsinized, then replated for two more passages in T-75 flasks. Cells are then trypsinized, washed and counted, diluted to $1 \times 10^5$ cells/mL in cDMEM and Ponasterone A added to a final concentration of 1 ug/mL, and seeded onto a 96-well plate at a density of 20,000 per well. Cells are incubated overnight in 37° C./5% $CO_2$ incubator, and should be at about 70-80% confluency.

Prepare a dilution series of test samples and control plasma samples in a dilution-plate (a 96-well U-bottomed tissue culture plate). Prepare a 3.1-fold (half-log) serial dilution of FACT Control plasma using FBS as the diluent. The dilution range depends on the FACT plasma. Recommended are at least six consecutive dilutions, typically between 1:10 to 1:3160.

Prepare a 3.1-fold serial dilution of the test sample using FBS as the diluent. The range of the dilution depends on the sample: Recommended dilutions are 1:1 to 1:316 for a baseline (pre-administration) samples, 1:10 and above for post-AAV administration samples.

Transfer 18 μL of above dilutions from the dilution plate to a second 96-well pre-assay plate. Prepare a working concentration of AAV luciferase vector by diluting the AAV luciferase vector to $8 \times 10^7$-$2 \times 10^9$ vg/mL in DMEM—do not use cDMEM or any diluent containing bovine serum. A volume of 0.5 mL diluted vector is sufficient for one full assay plate.

Prepare a mix of the vector with the diluted test and control samples to produce the 'neutralized' samples. Transfer the diluted vector to a 12-channel reservoir. Transfer 18 μL of the diluted vector from the reservoir to the 18 μL of each of the dilutions of the test and control samples in the pre-assay plate. Mix 18 μL of the diluted vector with 18 μL of FBS for the vector only control ("V+FBS"). Add 18 μL of FBS to one well in the pre-assay plate as "Blank." Incubate the pre-assay plate at 37° C. for one hour.

After incubation, transfer 7.5 μL of the 'neutralized' test sample dilutions, 'neutralized' control plasma dilutions, V+FBS control and Blank FBS to the assay plate in triplicates. Incubate the assay plate overnight in the 37° C./5% $CO_2$ incubator.

For cell lysis and measurement of luciferase activity, prepare enough lysis buffer (5 mL is sufficient for one plate) in a 15 or 50 mL conical tube, and enough assay buffer (7 mL is enough for one plate) in a 15 or 50 mL conical tube as described. At 20 to 24 hours post-transduction, wash cells once with PBS. Aspirate the cell-culture supernatant using a multi-channel pipette. Add 200 μL of the PBS to the cells, taking care not to disturb the cell-monolayer. Aspirate the wash and add 40 μL of lysis buffer per well, incubate the plate for 15 min at room temperature.

Turn the Luminometer and load the assay buffer to the designated area, prime the injector and load the cell plate (Promega luciferase protocol). Measure the luciferase activities and save all the readings in Excel. Parameters for luminometer: Integration time, 2 sec, Delay between last operation and this injection: 0 sec, Injection volume: 50 ul, Injection rate: 333 ul/sec, Delay between injection and measurement: 1 sec.

For calculation of anti-AAV neutralizing antibody titer, calculate the average raw luciferase-BLANK values from triplicates wells in Excel sheet and determine the luciferase % expression:

% luciferase expression=[(Test sample luciferase reading−BLANK)/(V-FBS luciferase reading−BLANK)]×100.

% luciferase inhibition=100−% luciferase expression

The neutralizing titer of the sample is determined as the highest dilution which results in 50% or greater inhibition of luciferase expression. The NAb titer is reported as a dilution range. For example, if 50% or greater inhibition is observed at the 1:10 dilution of the sample, the titer is reported as a range of 1:10 to 1:31

Operator Variation: Operator variability was evaluated based on the outcome of multiple AAV NAb determinations performed by Operators 1 and 2 on the same set of human serum samples on different days. Operators were not blinded to sample number.

Operator 1 performed the NAb assay on the 9 serum samples 6 times on different days. The FACT plasma was tested a total of 18 times on 6 different days.

Operator 2 performed the NAb assay on the 9 serum samples 5 times on different days. The FACT plasma was tested a total of 15 times on 5 different days.

Cell passage number was recorded and used for the results analysis. Finally, the anti-AAV8 NAb titer of the FACT plasma was determined after multiple freeze-thaw cycles to evaluate the changes in anti-AAV NAb associated with sample handling.

TABLE 1

| | Assay plate layout: | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | FACT (1:10) | | | Sample X (1:1) | | | Sample Y (1:1) | | | Sample Z (1:1) | | |
| B | FACT (1:31.6) | | | Sample X (1:3.16) | | | Sample Y (1:3.16) | | | Sample Z (1:3.16) | | |

TABLE 1-continued

Assay plate layout:

|   | 1 | 2 | 3 | 4 | 5 | 6 | 7 | 8 | 9 | 10 | 11 | 12 |
|---|---|---|---|---|---|---|---|---|---|---|---|---|
| C | FACT (1:100) | | | Sample X (1:10) | | | Sample Y (1:10) | | | Sample Z (1:10) | | |
| D | Max Signal | | | Sample X (1:31.6) | | | Sample Y (1:31.6) | | | Sample Z (1:31.6) | | |
| E | Background | | | Sample X (1:100) | | | Sample Y (1:100) | | | Sample Z (1:100) | | |
| F | FACT (1:316) | | | Sample X (1:316) | | | Sample Y (1:316) | | | Sample Z (1:316) | | |
| G | FACT (1:1000) | | | Sample X (1:1000) | | | Sample Y (1:1000) | | | Sample Z (1:1000) | | |
| H | FACT (1:3160) | | | Sample X (1:3160) | | | Sample Y (1:3160) | | | Sample Z (1:3160) | | |

Sample dilutions are indicated between parentheses. Max Signal wells contain virus incubated with sample diluent only. Background wells contain diluent only. A maximum of three unknown samples are tested in a 96 well plate. The assay plate layout indicated here is identical to that used during performance of the assay.

Example 4

This example includes a description of assay results for detecting and/or quantifying anti-AAV antibodies.

Signal intensity as a function of cell passage number: A total of 33 plates were seeded and used for AAV NAb testing in this study. Maximum and minimum reporter signal intensity was measured as a function of the cell passage number.

A decrease in the maximum reporter gene signal (Max signal) was observed at increasing number of cell passages (FIG. 1A), which did not seem to affect the results of the assay, i.e. the NAb titer was identical for samples assayed regardless of cell passage number up to 25 passages, and all assays met requirements for a successful assay. Note that cells used in the current assay were never passaged more than 25 times. For purposes of the NAb assay, cells should be at less than or equal to 25 passages.

Figure 1B:
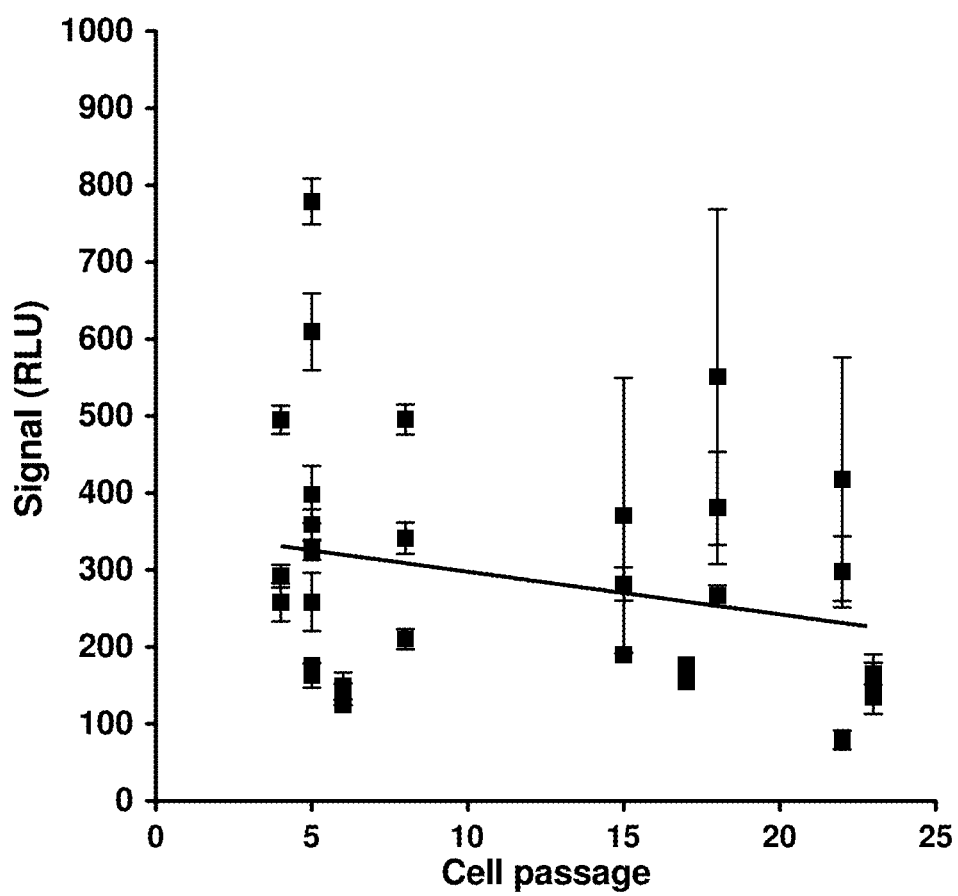
FIG. 1B shows luciferase reporter gene Background Signal as a function of number of cell passages. Statistical analysis performed usng GraphPad Prism Version 5.0b. Linear regression: R2 curve 0.04720, p=0.0308, the slope of the curve is significantly non-zero. Additional statistical analysis was performed by comparing the mean of Background Signal (RLU) obtained with cells from passages 1-12 with that of passages 13-25. For this purpose, a two-tailed unpaired t test was used. Mean+/−standard error of the mean: passage 1-12, 320+/−24, n=54; passage 13-25, 252+/−27, n=45, p=0.0651.

Background signal also decreased with cell passage number (FIG. 1B). However, the mean signal for cell passage 1-12 vs. 13-25 was not statistically different.

Operator Variability: The AAV NAb titer of the specific lot of FACT plasma used for these analyses, evaluated routinely in the laboratory over the course of several months, is 1:100-1:316 for AAV8 vectors. NAb titers ≥ or ≤½ log from the mean value are rejected. The standard approach to investigation of rejected runs is to confirm that none of the reagents are expired and that the maintenance of key equipment including the luminometer is up-to-date. Experience indicates that a specific cause is rarely found for out-of-range assays; most likely it reflects the inherent variability of a cell-based assay.

Operator 1: In the set of determinations performed by Operator 1 (Table 2A) the anti-AAV8 NAb titer of the FACT control plasma was measured 18 times in six separate studies.

16/18 times the FACT plasma gave a titer of 1:100-1:316;

1/18 times (Plate 2, Day 4) the titer was measured ½ log lower, 1:31.6-1:100, leading to the rejection of the assay run;

1/18 times (Plate 3, Day 6) the titer was measured ½ log higher, 1:316-1:1000, leading to the rejection of the assay run.

TABLE 2A

Anti-AAV Titers in FACT plasma samples (Operator 1)

|  | Day 1 | Day 2 | Day 3 | Day 4 | Day 5 | Day 6 |
|---|---|---|---|---|---|---|
| Plate 1 | 1:100-1:316 | 1:100-1:316 | 1:100-1:316 | 1:100-1:316 | 1:100-1:316 | 1:100-1:316 |
| Plate 2 | 1:100-1:316 | 1:100-1:316 | 1:100-1:316 | 1:31.6-1:100 | 1:100-1:316 | 1:100-1:316 |
| Plate 3 | 1:100-1:316 | 1:100-1:316 | 1:100-1:316 | 1:100-1:316 | 1:100-1:316 | 1:316-1:1000 |

A total of 9 human serum samples were tested for anti-AAV8 NAb on six different days. Results are summarized in Table 2B. The gray-shaded areas represent the assay runs that have been excluded from the analysis because the FACT plasma control NAb titer was different from the historical range.

No variability between titers was observed for Samples 1, 2, 3, 5, and 7, which scored negative (<1:1) on all test days. For Samples 4 and 9, approximately 1 log variation was observed over 5 test days with titers ranging from <1:1 to 1:3.1-1:10 and 1:3.1-1:10 to 1:31.6-1:100, respectively. For Sample 6, a half log variation was observed; this sample scored negative on all test days but Day 5, in which it scored 1:1-3.1. A half log variation in titers was also observed for Sample 8 with titers ranging from 1:316-1:1000 to 1:1000-1:3160.

Each sample consistently scored either above or below the threshold for study eligibility, except for Sample 9, which scored above the threshold on Days 1-4 (ineligible) and below the threshold on Day 5 (eligible).

TABLE 2B

Anti-AAV titers in human serum samples (Operator 1)

|  | Day 1 | Day 2 | Day 3 | Day 4 | Day 5 | Day 6 |
|---|---|---|---|---|---|---|
| Sample 1 | <1:1 | <1:1 | <1:1 | <1:1 | <1:1 | <1:1 |
| Sample 2 | <1:1 | <1:1 | <1:1 | <1:1 | <1:1 | <1:1 |
| Sample 3 | <1:1 | <1:1 | <1:1 | <1:1 | <1:1 | <1:1 |
| Sample 4 | <1:1 | <1:1 | 1:1-1:3.1 | 1:1-1:3.1 | 1:3.1-1:10 | 1:1-1:3.1 |
| Sample 5 | <1:1 | <1:1 | <1:1 | <1:1 | <1:1 | <1:1 |
| Sample 6 | <1:1 | <1:1 | <1:1 | <1:1 | 1:1-1:3.1 | <1:1 |
| Sample 7 | <1:1 | <1:1 | <1:1 | <1:1 | <1:1 | <1:1 |
| Sample 8 | 1:1000-1:3160 | 1:1000-1:3160 | 1:316-1:1000 | 1:1000-1:3160 | 1:316-1:1000 | 1:316-1:1000 |
| Sample 9 | 1:10-1:31.6 | 1:31.6-1:100 | 1:31.6-1:100 | 1:10-1:31.6 | 1:3.1-1:10 | 1:10-1:31.6 |

Samples 1-3 were on Plate 1; Samples 4-6 were on Plate 2; Samples 7-9 were on Plate 3

Operator 2: In the part of the study performed by Operator 2 (Table 3A) the anti-AAV8 NAb titer of the FACT control plasma was measured 15 times in five separate experiments.
- 13/15 times the FACT plasma gave a titer of 1:100-1:316;
- 1/15 times (Plate 3, Day 3) the titer was measured ½ log higher, 1:316-1:1000, leading to the rejection of the assay run.
- 1/15 times (Plate 3, Day 5) the titer was measured ½ log lower, 1:31.6-1:100, leading to the rejection of the assay run.

TABLE 3

AAnti-AAV Titers in FACT plasma samples (Operator 2)

|  | Day 1 | Day 2 | Day 3 | Day 4 | Day 5 |
|---|---|---|---|---|---|
| Plate 1 | 1:100-1:316 | 1:100-1:316 | 1:100-1:316 | 1:100-1:316 | 1:100-1:316 |
| Plate 2 | 1:100-1:316 | 1:100-1:316 | 1:100-1:316 | 1:31.6-1:100 | 1:100-1:316 |
| Plate 3 | 1:100-1:316 | 1:100-1:316 | 1:316-1:1000 | 1:100-1:316 | 1:31.6-1:100 |

A total of 9 human serum samples were tested for anti-AAV8 NAb on five different days. Results are summarized in Table 3B. The shaded areas represent the assay runs that have been excluded from the analysis because the FACT plasma control NAb titer was different from the historical range.

Samples 1, 2, 3, 5, 6, with negative anti-AAV8 NAb titers (<1:1), and Sample 4, with a titer of 1:1-1:3.1, consistently gave the same titers across all five test days. Higher titer samples, Samples 8 and 9, were also consistent across test days; Sample 8 scored 1:100-1:316 and Sample 9 scored 1:10-1:31.6. Sample 7 scored negative (<1:1) on all test days with the exception of Day 2, in which it scored 1:1-1:3.1, a half log variation.

Each sample consistently scored either above or below the threshold for study eligibility.

TABLE 3B

Anti-AAV titers in human serum samples (Operator 2)

|  | Day 1 | Day 2 | Day 3 | Day 4 | Day 5 |
|---|---|---|---|---|---|
| Sample 1 | <1:1 | <1:1 | <1:1 | <1:1 | <1:1 |
| Sample 2 | <1:1 | <1:1 | <1:1 | <1:1 | <1:1 |
| Sample 3 | <1:1 | <1:1 | <1:1 | <1:1 | <1:1 |
| Sample 4 | 1:1-1:3.1 | 1:1-1:3.1 | 1:1-1:3.1 | 1:1-1:3.1 | 1:1-1:3.1 |
| Sample 5 | <1:1 | <1:1 | <1:1 | <1:1 | <1:1 |
| Sample 6 | <1:1 | <1:1 | <1:1 | <1:1 | <1:1 |
| Sample 7 | <1:1 | 1:1-1:3.1 | <1:1 | <1:1 | <1:1 |
| Sample 8 | 1:100-1:316 | 1:100-1:316 | 1:316-1:1000 | 1:100-1:316 | 1:316-1:1000 |
| Sample 9 | 1:10-1:31.6 | 1:10-1:31.6 | 1:100-1:316 | 1:10-1:31.6 | 1:3.1-1:10 |

Samples 1-3 were on Plate 1; Samples 4-6 were on Plate 2; Samples 7-9 were on Plate 3

Figure 2:
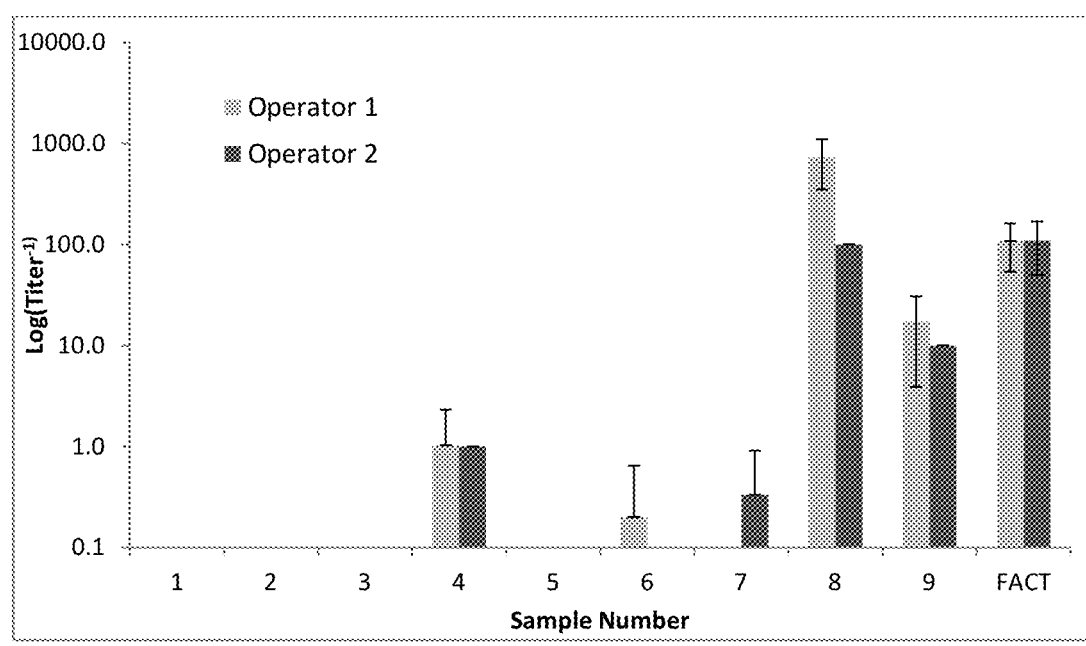
FIG. 2 shows mean NAb titers for human serum samples for operators 1 and 2. Error bars show ± a standard deviation.
Figure 3:
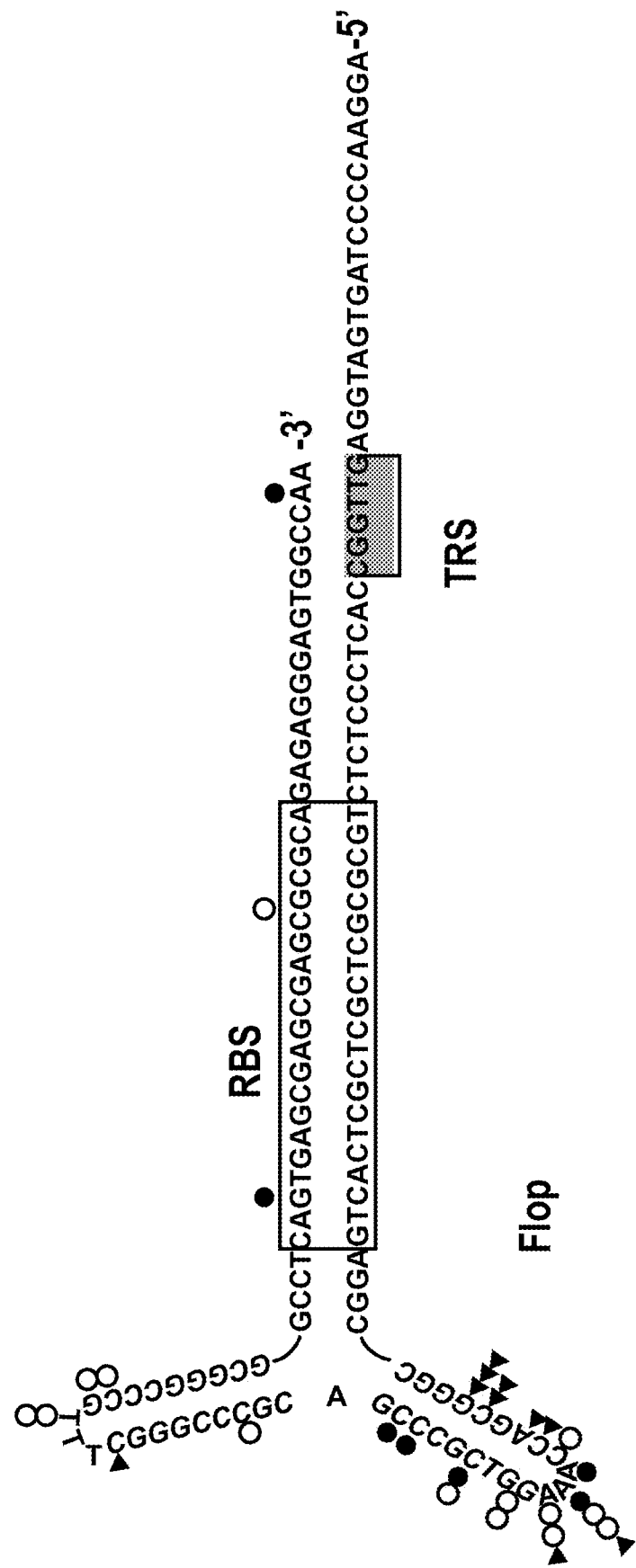
FIG. 3 shows a structure of AAV2 ITR with a mutated TRS sequence (SEQ ID NO:1): "CGGTTG" as indicated. RBS: Rep Binding Sequence; Flop/Flip: ITR (analogous to+/strain).
Figure 4:
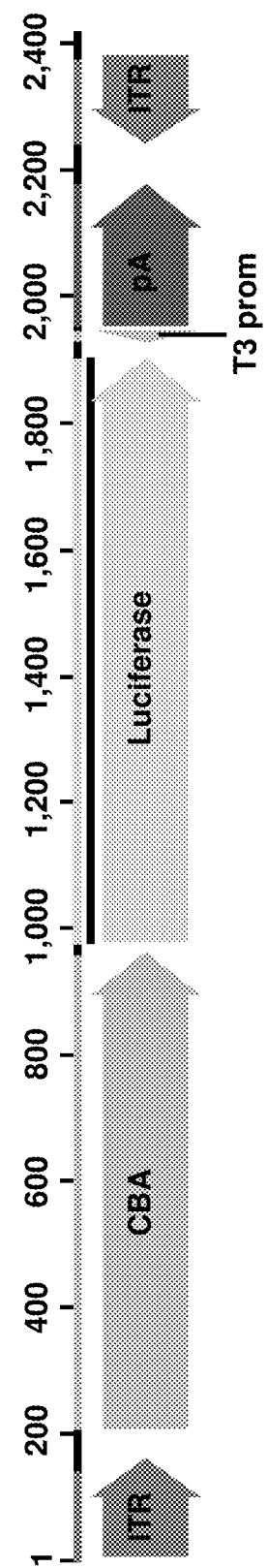
FIG. 4 shows a generic plasmid construct structure with a luciferase reporter transgene. CBA: chicken beta-actin promoter; pA: polyadenylation.

Interoperator Variability: Mean AAV NAb titers for each sample as measured by Operators 1 and 2 are presented in Table 4 and FIG. 2. Means were calculated using the reciprocal of the lower value of the reported titer range. For example, if the titer for a sample in a given run was reported as 1:3.1-1:10, a value of 3.1 was used for calculating the mean. For titers reported as <1:1, a value of 0 was used.

No inter-operator variability was observed for Samples 1, 2, 3, 4 or 5. Some inter-operator variability was observed for Samples 6, 7, 8, and 9, although the difference between operator means was not greater than 1 log for any sample. Mean FACT titers were practically the same between operators, differing by only 0.01 log (calculation of mean FACT titer included rejected runs where FACT titer was different than its historical range).

TABLE 4

Mean Titers and Standard Deviations for Operators 1 and 2

|  | Operator 1 | | Operator 2 | |
|---|---|---|---|---|
|  | Mean | Standard Deviation | Mean | Standard Deviation |
| Sample 1 | 0 | 0 | 0 | 0 |
| Sample 2 | 0 | 0 | 0 | 0 |
| Sample 3 | 0 | 0 | 0 | 0 |
| Sample 4 | 1.0 | 1.3 | 1.0 | 0 |
| Sample 5 | 0 | 0 | 0 | 0 |
| Sample 6 | 0.2 | 0.5 | 0 | 0 |
| Sample 7 | 0 | 0 | 0.3 | 0.6 |
| Sample 8 | 726.4 | 374.6 | 100.0 | 0 |
| Sample 9 | 17.3 | 13.4 | 10.0 | 0 |
| FACT | 108.2 | 109.8 | 109.8 | 59.7 |

Effect of Freeze-Thaw Cycles: The effect of repeated freeze-thaw cycles on the AAV NAb titer was evaluated on the FACT plasma positive control. Samples were subjected to up to six freeze-thaw cycles (thaw at 37° C. and freeze in ethanol/dry ice bath, with interim storage at −80° C.) and the anti-AAV8 NAb titer measured. The test was repeated twice. Note that test samples are also stored at −80° C., but are thawed on ice (0° C.). Results of the freeze-thaw test are summarized in Table 5. No variations in AAV NAb titer were measured after up to six freeze-thaw cycles.

TABLE 5

Effect of freeze-thaw on anti-AAV8 NAb titer of FACT control plasma.

| Freeze thaw cycles | First run NAb titer (cell passage 3) | Second run NAb titer (cell passage 4) |
|---|---|---|
| 0 | 1:100-1:316 | 1:100-1:316 |
| 1 | 1:100-1:316 | 1:100-1:316 |
| 2 | 1:316-1:1000 | 1:100-1:316 |
| 3 | 1:100-1:316 | 1:100-1:316 |
| 4 | 1:100-1:316 | 1:100-1:316 |
| 5 | 1:100-1:316 | 1:100-1:316 |
| 6 | 1:100-1:316 | 1:100-1:316 |

Example 5

This example includes a description of conclusions based upon the AAV antibody assay.

Within 25 passages from the initial thawing of the cells used in the NAb assay, a significant decrease in the maximum signal of the luciferase signal was observed. However, this decrease did not appear to affect the test results, i.e. the AAV NAb titer was identical for samples assayed regardless of cell passage number up to 25 passages, and all assays met requirements for a successful assay.

Six cycles of freeze-thaw do not affect the NAb titer of control plasma sample measured in the assay. The control plasma used in this assay is aliquoted and frozen upon receipt, and thawed aliquots are not refrozen.

A limited variability in the NAb titer was observed across several determinations on the same set of samples (inter-assay variability). A higher variability was measured for samples with a medium to high NAb titer, while lower variability was observed in low-titer NAb samples.

Similarly, higher variability in the NAb titer was observed across operators (inter-operator variability) for samples with a medium to high NAb titer, while lower variability was observed in low-titer NAb samples.

Given that the NAb titer threshold for inclusion in current AAV-mediated gene transfer trials is <1:5, an ambiguous result was observed only for Sample 9, which scored >1:5 in 7/8 test runs (not eligible for enrollment in the study) and <1:5 in 1/8 runs (eligible for enrollment in the study). If this had been an actual subject sample, the titer of <1:5 would have prompted repeat testing.

These results indicate that the NAb assay is a reliable test to measure anti-AAV NAb titers in human serum (or plasma) samples. Such an assay can be used to identify subjects with low anti-AAV titers prior to enrollment in AAV gene transfer trials, and/or to monitor AAV titers during or following AAV-mediated gene transfer.

What is claimed is:

1. A method for quantifying neutralizing antibodies that bind to AAV, comprising:
   (a) providing infectious recombinant AAV particles that encapsidate a recombinant vector, wherein (i) the vector comprises a reporter transgene, wherein the reporter transgene encodes a protein that provides an enzymatic, colorimetric, fluorescent, luminescent, chemiluminescent, or electrochemical signal, (ii) the reporter transgene comprises a self-complementary genome, and (iii) the reporter transgene is operably linked to one or more expression regulatory elements and flanked by one or more flanking elements;
   (b) providing a biological sample from a subject for quantifying neutralizing antibodies that bind to AAV;
   (c) providing human embryonic kidney (HEK) cells with a passage number up to 25 passages after initial thawing;
   (d) contacting or incubating the infectious recombinant AAV particles of (a) with the biological sample of (b) thereby producing a resulting mixture (M);
   (e) contacting the mammalian cells of (c) with resulting mixture (M) under conditions in which the infectious recombinant AAV particles of (a) can infect and express the reporter transgene in said cells;
   (f) measuring expression of the reporter transgene; and
   (g) comparing said reporter transgene expression of (f) to reporter transgene of a negative (−) control lacking neutralizing antibodies that bind to AAV.

2. The method of claim 1, wherein the HEK cells provide nucleic acid sequences encoding helper functions for AAV replication and/or genomic integration.

3. The method of claim 1, wherein the HEK cells can be infected with AAV particles comprising a VP1, VP2 or VP3 protein sequence 99% or more identical to a VP1, VP2 or VP3 protein sequence of AAV serotype AAV1, AAV2, AAV3, AAV4, AAV5, AAV6, AAV7, AAV8, AAV9, AAV10, AAV11, AAV12, or Rh10.

4. The method of claim 1, wherein the HEK cells comprise HEK-293 cells.

5. The method of claim 1, wherein the HEK cells express adenovirus E4 gene.

6. The method of claim 1, wherein the HEK cells comprise 2V6.11 cells.

7. The method of claim 1, wherein the reporter transgene comprises a luciferase gene.

8. The method of claim 7, wherein the luciferase gene comprises a renilla luciferase or a firefly luciferase gene.

9. The method of claim 1, wherein the AAV vector comprises an AAV1, AAV2, AAV3, AAV4, AAV5, AAV6, AAV7, AAV8, AAV9, AAV10, AAV11, AAV12, or Rh10 vector.

10. The method of claim 1, wherein the expression regulatory elements comprise a promoter and/or enhancer nucleic acid sequence operable in mammalian cells.

11. The method of claim 1, wherein the flanking element(s) comprises one or more AAV inverted terminal repeat sequences (ITRs).

12. The method of claim 1, wherein the flanking element(s) comprises a mutated or variant AAV ITR that is not processed by AAV Rep protein.

13. The method of claim 1, wherein the flanking element(s) comprises a mutated or variant AAV ITR that allows or facilitates formation of the self-complementary reporter transgene genome into a double strand inverted repeat sequence structure in the infectious recombinant AAV particles.

14. The method of claim 13, wherein the mutated, modified or variant AAV ITR has a deleted D sequence, and/or a mutated, modified or variant terminal resolution site (TRS) sequence.

15. The method of claim 1, wherein the recombinant vector comprises a first inverted terminal repeat (ITR) of an AAV; a promoter operable in mammalian cells; the reporter transgene; a polyadenylation signal; and optionally a second ITR of an AAV.

16. The method of claim 1, wherein the infectious recombinant AAV particles comprise an AAV serotype that infects primates.

17. The method of claim 1, wherein the infectious recombinant AAV particles comprise a VP1, VP2 or VP3 protein sequence 99% or more identical to a VP1, VP2 or VP3 protein sequence of AAV serotype AAV1, AAV2, AAV3, AAV4, AAV5, AAV6, AAV7, AAV8, AAV9, AAV10, AAV11, AAV12, or Rh10.

18. The method of claim 1, wherein the biological sample comprises human serum or human plasma.

19. The method of claim 1, wherein the subject is a mammal.

20. The method of claim 1, wherein the subject is a human.

21. The method of claim 1, wherein the subject suffers from a disorder due to insufficient expression or activity of a protein.

22. The method of claim 1, wherein the subject suffers from a disorder due to expression or activity of an abnormal, aberrant or undesirable protein.

23. The method of claim 1, wherein the subject suffers from a genetic disorder.

24. The method of claim 1, wherein the subject suffers from cystic fibrosis hemophilia A or hemophilia B with or without inhibitors, thalassemia, anemia, Alzheimer's disease, Parkinson's disease, Huntington's disease, amyotrophic lateral sclerosis (ALS), epilepsy, lysosomal storage diseases, Wilson's or Menkes disease, lysosomal acid lipase deficiency, cancer, type 1 or type 2 diabetes, Gaucher's disease, Hurler's disease, adenosine deaminase deficiency, a glycogen storage disease, RPE65 deficiency, choroideremia hepatitis B, hepatitis C, HIV, or a bacterial or fungal infection.

25. The method of claim 1, further comprising entering or including the amount of antibodies that bind to AAV in the biological sample into a report associated with said subject.

26. The method of claim 1, wherein the biological sample is diluted prior to contact or incubating with the infectious recombinant AAV particles of (a).

27. The method of claim 1, wherein a plurality of dilutions of the biological sample are analyzed.

28. The method of claim 1, wherein the biological sample is diluted between 1:1 and 1:500 prior to contacting or incubating with the infectious recombinant AAV particles of (a).

29. The method of claim 1, wherein the HEK cells are contacted with the resulting mixture (d) for a period of 6-48 hours.

30. The method of claim 1, wherein the HEK cells are lysed prior to measuring expression of the reporter transgene.

31. The method of claim 1, wherein the biological sample has been heat inactivated.

32. The method of claim 1, further comprising comparing said reporter transgene expression of (f) to reporter transgene of a control having a predetermined amount of antibodies that bind to AAV.

33. The method of claim 1, wherein the HEK cells can be infected with AAV particles comprising a VP1, VP2 or VP3 protein sequence identical to a VP1, VP2 or VP3 protein sequence of AAV serotype AAV1, AAV2, AAV3, AAV4, AAV5, AAV6, AAV7, AAV8, AAV9, AAV10, AAV11, AAV12, or Rh10.

34. The method of claim 1, wherein the infectious recombinant AAV particles comprise a VP1, VP2 or VP3 protein sequence identical to a VP1, VP2 or VP3 protein sequence of AAV serotype AAV1, AAV2, AAV3, AAV4, AAV5, AAV6, AAV7, AAV8, AAV9, AAV10, AAV11, AAV12, or Rh10.

* * * * *